(12) United States Patent
Fukui et al.

(10) Patent No.: US 10,271,734 B2
(45) Date of Patent: Apr. 30, 2019

(54) PHOTOACOUSTIC APPARATUS

(71) Applicant: CANON KABUSHIKI KAISHA, Tokyo (JP)

(72) Inventors: Tatsuki Fukui, Yokohama (JP); Atsushi Takahashi, Kyoto (JP); Satoshi Yuasa, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 144 days.

(21) Appl. No.: 15/080,805

(22) Filed: Mar. 25, 2016

(65) Prior Publication Data

US 2016/0287085 A1    Oct. 6, 2016

(30) Foreign Application Priority Data

Apr. 1, 2015 (JP) .................................. 2015-075393

(51) Int. Cl.
*A61B 5/00* (2006.01)

(52) U.S. Cl.
CPC .......... *A61B 5/0095* (2013.01); *A61B 5/7203* (2013.01); *A61B 2576/00* (2013.01); *A61B 2576/02* (2013.01)

(58) Field of Classification Search
CPC . A61B 5/0095; A61B 5/7203; A61B 2576/00; A61B 2576/02
USPC ................................................ 600/437–480
See application file for complete search history.

(56) References Cited

U.S. PATENT DOCUMENTS

| | | | |
|---|---|---|---|
| 6,317,623 B1 | 11/2001 | Griffiths et al. | |
| 6,939,302 B2 | 9/2005 | Griffiths et al. | |
| 8,652,441 B2 | 2/2014 | Fukui et al. | 424/9.6 |
| 2002/0055682 A1 | 5/2002 | Griffiths et al. | |
| 2010/0191109 A1* | 7/2010 | Fukutani | A61B 5/0059 600/437 |
| 2011/0117023 A1 | 5/2011 | Yamauchi et al. | 424/9.1 |

(Continued)

FOREIGN PATENT DOCUMENTS

| | | |
|---|---|---|
| CN | 102481108 A | 5/2012 |
| CN | 103492871 A | 1/2014 |

(Continued)

OTHER PUBLICATIONS

X. Wang et al., "Noninvasive photoacoustic angiography of animal brains in vivo with near-infrared light and an optical contrast agent", *Optics Letters*, vol. 29, No. 7 pp. 730-732 (Apr. 1, 2004).

(Continued)

*Primary Examiner* — Sanjay Cattungal
(74) *Attorney, Agent, or Firm* — Venable LLP

(57) ABSTRACT

A photoacoustic apparatus comprises a light source; an irradiation unit configured to radiate light from the light source to an object that contains a contrast agent; a receiving unit configured to receive acoustic waves generated when the contrast agent absorbs the light radiated by the irradiation unit and output an electrical signal; a correction processing unit configured to correct a signal strength of the electrical signal, based on a temporal change in a concentration of the contrast agent contained in the object; and an acquiring unit configured to acquire characteristics information on the object, based on the electrical signal that has been corrected by the correction processing unit.

18 Claims, 7 Drawing Sheets

(56) References Cited

U.S. PATENT DOCUMENTS

| | | | |
|---|---|---|---|
| 2012/0197117 A1 | 8/2012 | Picot et al. | 600/438 |
| 2014/0046165 A1 | 2/2014 | Fukutani | |
| 2014/0161227 A1 | 6/2014 | Flohr et al. | 378/62 |
| 2014/0198606 A1* | 7/2014 | Morscher | A61B 5/0095 367/11 |
| 2015/0025373 A1 | 1/2015 | Kim et al. | |
| 2015/0178959 A1* | 6/2015 | Huang | G06T 11/006 600/407 |
| 2015/0359512 A1* | 12/2015 | Boctor | G01S 15/8997 600/444 |
| 2016/0022236 A1 | 1/2016 | Ohishi | 600/431 |

FOREIGN PATENT DOCUMENTS

| | | |
|---|---|---|
| CN | 103860185 A | 6/2014 |
| JP | 2002-537933 A | 11/2002 |
| JP | 2010-075634 | 4/2010 |
| JP | 2014-200593 | 10/2014 |
| WO | 00/53096 A1 | 9/2000 |

OTHER PUBLICATIONS

G.R. Cherrick et al., "Indocyanine Green: Observations on Its Physical Properties, Plasma Decay, and Hepatic Extraction", *Journal of Clinical Investigations*, vol. 39, No. 4, pp. 592-600 (Apr. 1960).

European Extended Search Report dated Aug. 5, 2016, in counterpart European patent application 16162754.2 (in English).

Office Action dated Dec. 26, 2018, in counterpart application CN 201610203761.6 (16 pages).

Office Action dated Jan. 15, 2019, in counterpart application JP 2015-075393 (6 pages).

\* cited by examiner

PHOTOACOUSTIC APPARATUS

BACKGROUND OF THE INVENTION

Field of the Invention

The present invention relates to a photoacoustic apparatus.

Description of the Related Art

Researches on optical imaging techniques that irradiate a living body with light emitted from a light source such as a laser and reconstruct, as an image, information on the inside of the living body obtained based on the incident light have progressed actively in a medical field. A photoacoustic tomography (PAT) is one of the optical imaging techniques. According to the photoacoustic imaging technique, an object is irradiated with pulsed light generated from a light source. The energy of the pulsed light propagated and diffused in the living body is absorbed in the tissues of the living body and acoustic waves (typically ultrasound waves) are generated. The generated acoustic waves propagate through the living body and are received by a probe and detected as electrical signals. An information processing device performs a mathematical analysis process (an image reconstruction process) on the obtained signals to visualize information related to optical characteristic values inside an object. In this way, information on the inside of the object (for example, an initial acoustic pressure, an optical characteristic value (particularly, optical energy absorption density and absorption coefficient), and a distribution thereof) can be obtained. The obtained information can be used for specifying a distribution of absorbers in the living body, the location of malignant tumors, and the like.

In photoacoustic measurement, initial acoustic pressure $P_0$ of acoustic waves generated from a light absorber in an object can be expressed by the following equation.

$$P_0 = \Gamma \cdot \mu_a \cdot \Phi \qquad (A)$$

Here, $\Gamma$ is a Gruneisen coefficient which is a division of the product of a volume expansion coefficient $\beta$ and the square of the speed of sound c by the specific heat capacity $C_p$ at constant pressure. It is known that $\Gamma$ takes an almost constant value if the object is determined. $\mu_a$ is an absorption coefficient of the light absorber, and $\Phi$ is a light quantity at the position of the light absorber (a quantity of light radiated to the light absorber; also referred to as light fluence). The initial acoustic pressure $P_0$ generated by the light absorber inside an object propagates through the object as acoustic waves which are detected by a probe disposed on the surface of the object. A change with time in the acoustic pressure of the detected acoustic waves is measured, and the initial acoustic pressure distribution $P_0$ can be calculated from the measurement results using an image reconstruction method such as a back-projection method. When the calculated initial acoustic pressure distribution $P_0$ is divided by the Gruneisen coefficient $\Gamma$, a distribution of the product of $\mu_a$ and $\Phi$ (that is, an optical energy density distribution) can be obtained. Moreover, if a light quantity distribution $\Phi$ inside an object is known, the absorption coefficient distribution $\mu_a$ can be obtained by dividing the optical energy density distribution by the light quantity distribution $\Phi$. That is, when a light absorber having known optical characteristics in relation to light radiated to the inside of an object is injected as a contrast agent, acoustic waves corresponding the abundance of the contrast agent can be acquired.

In photoacoustic measurement, pulsed light generated from a light source is radiated to an object. Acoustic waves are generated from a sound source that absorbed the energy of light propagated and diffused inside the object. The generated acoustic waves are detected by a probe disposed around the object. A spatial distribution image of the sound source is obtained by reconstructing the detected acoustic waves. In this case, in order to guarantee the accuracy of the image, a series of operations of irradiating an object with pulsed light generated from a light source and receiving photoacoustic waves propagating from the object may be performed repeatedly. Thus, in this case, a certain period is required until the last acoustic waves are received after light irradiation for photoacoustic measurement is started and acoustic waves are received. That is, a time lag occurs between the first photoacoustic measurement (the first light irradiation and the first acoustic wave reception) and the last photoacoustic measurement.

On the other hand, when a living body is an object, the blood (hemoglobin) is one of the substances which have highly absorptive to near-infrared light. That is, information on the spatial distribution of the blood can be obtained by performing photoacoustic measurement on the living body using near-infrared light. However, sufficiently high S/N ratio of signals cannot be guaranteed by the abundance of hemoglobin only, and sufficiently high contrast may not be obtained. In this case, when a light absorber is further injected into the blood vessel as a contrast agent, a PAT image (also referred to as a photoacoustic image) in which the contrast is enhanced depending on the density of a light absorber present in a blood vessel portion can be obtained. As conditions of a contrast agent usable in a living body, the contrast agent is required to have such optical characteristic that the contrast agent can better absorb light in a wavelength region in which light is highly transmissive in a living body. Indocyanine green (hereinafter sometimes abbreviated as ICG) can be ideally used as an example of the contrast agent that satisfies such conditions. Since ICG is a material approved for medical use and is a light absorber that can better absorb light in a near-infrared wavelength region having a high transmissive property in a living body, ICG can be used as a preferable contrast agent for photoacoustic measurement of living bodies. In Optics Letters, Vol. 29, Issue 7, pp. 730-732 (2004), ICG was injected into a mouse to investigate the retention of ICG in the blood.

However, it is known that ICG is rapidly cleared from the blood. Specifically, it is reported that the half-life of ICG in the blood is approximately 3 minutes (J Clin Invest., 1960 April; 39(4): p. 592-600). This means that, when ICG is used as a vascular contrast agent, the period in which ICG can function in the blood vessel is very short. Thus, the time lag that occurs means that, even if photoacoustic measurement started immediately after injection, a blood concentration of ICG decreases greatly in the period between the first acoustic wave acquisition time and the last signal acquisition time.

On the other hand, the strength of acoustic waves measured by a probe in angiography depends on the blood ICG concentration as in Equation A. Thus, when a light absorber such as ICG of which the blood concentration changes during measurement, a variation occurs in the acoustic waves received based on the period elapsed from injection into the blood and the accuracy of photoacoustic image decreases.

In view of the above problems, it is an object of the present invention to provide a photoacoustic apparatus capable of reducing the influence of a strength variation in acoustic waves based on a measurement period in photoacoustic measurement which uses a contrast agent.

SUMMARY OF THE INVENTION

The present invention in its one aspect provides a photoacoustic apparatus comprising a light source; an irradiation unit configured to radiate light from the light source to an object that contains a contrast agent; a receiving unit configured to receive acoustic waves generated when the contrast agent absorbs the light radiated by the irradiation unit and output an electrical signal; a correction processing unit configured to correct a signal strength of the electrical signal, based on a temporal change in a concentration of the contrast agent contained in the object; and an acquiring unit configured to acquire characteristics information on the object, based on the electrical signal that has been corrected by the correction processing unit.

Further features of the present invention will become apparent from the following description of exemplary embodiments with reference to the attached drawings.

DESCRIPTION OF THE EMBODIMENTS

Figure 1:
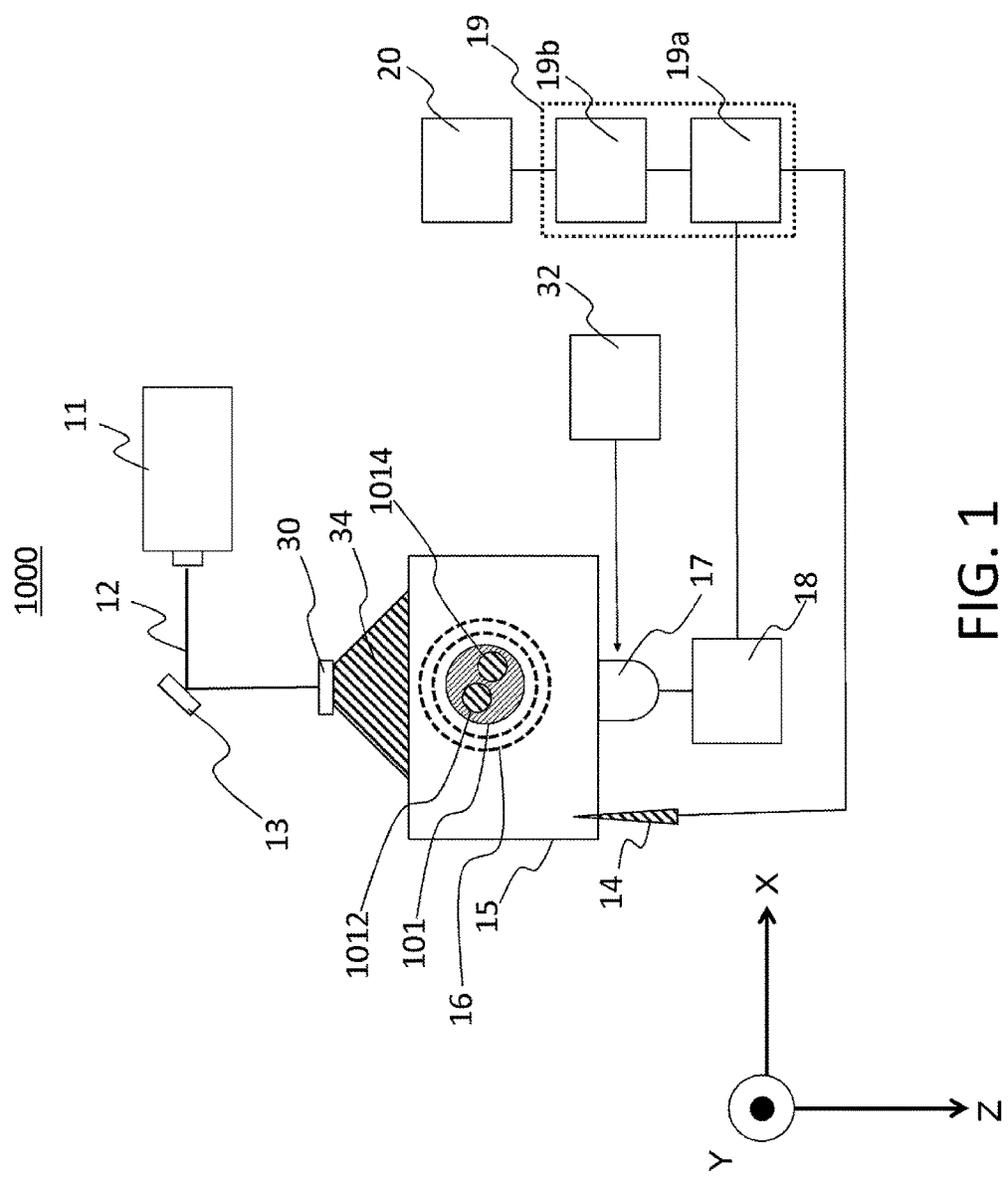
FIG. 1 is a block diagram illustrating Example 1 of a photoacoustic apparatus of the present invention.

Hereinafter, embodiments of the present invention will be described in detail with reference to the drawings. As a general rule, the same constituent elements will be denoted by the same reference numerals, and the description thereof will be omitted. Detailed calculation formula, calculation procedures, and the like described below are to be appropriately changed according to the configuration and various conditions of an apparatus to which the present invention is applied, and the scope of the present invention is not limited to those described below.

An object information acquiring apparatus of the present invention includes an apparatus which uses a photoacoustic effect to receive acoustic waves generated inside an object by irradiating the object with light (electromagnetic waves) such as near-infrared light to acquire object information as image data.

In the case of an apparatus which uses a photoacoustic effect, the acquired object information indicates a generation source distribution of acoustic waves generated by light irradiation, an initial acoustic pressure distribution inside the object, an optical energy absorption density distribution and an absorption coefficient distribution derived from the initial acoustic pressure distribution, or a concentration distribution of a substance that constitutes a tissue. Examples of the substance concentration distribution include an oxygen saturation distribution, a total hemoglobin concentration distribution, and an oxygenated or reduced hemoglobin concentration distribution.

Moreover, the characteristics information (for example, an initial acoustic pressure distribution, an optical energy absorption density distribution, an absorption coefficient distribution, and the like) of an object at a plurality of positions may be acquired as a 2-dimensional or 3-dimensional characteristics distribution. The characteristics distribution may be generated as image data indicating the characteristics information inside an object. The characteristics information of an object is also referred to as object information.

The acoustic wave referred in the present invention is typically an ultrasound wave and includes an elastic wave called a sound wave and an ultrasound wave. The acoustic wave generated by the photoacoustic effect is referred to as a photoacoustic wave or a light-induced ultrasound wave. A probe receives an acoustic wave generated inside an object.

Photoacoustic measurement may require a certain measurement period. For example, a series of operation of irradiating an object with light in a state in which a probe is fixed at a certain position and receiving acoustic waves may be performed repeatedly a plurality of number of times. Moreover, it is most ideal to dispose probes in all directions of 360° around an object, receive generated acoustic waves, and reconstruct a spatial distribution as an image. However, the shape and the structure of an object and the space in which probes are disposed are limited, it is very difficult to dispose probes in all directions around the object to perform photoacoustic measurement. Thus, practically, multi-probes disposed around an object are moved to a plurality of acoustic wave reception positions and acoustic waves are received at the respective acoustic wave reception positions (or light irradiation positions). According to this method, it is possible to obtain sufficient information for image reconstruction by acquiring acoustic waves from directions as broad as possible in relation to the object. In this manner, when multi-probes are moved during photoacoustic measurement to receive acoustic waves at a plurality of acoustic wave reception positions, a measurement time lag occurs until a series of operations of receiving acoustic waves from the object are completed. For example, the following problem occurs when the oscillation frequency of the pulsed light radiated to an object is 20 Hz, the number of integrations at the respective acoustic wave reception positions is 20 times, and measurement is conducted at 120 acoustic wave reception positions. That is, one photoacoustic measurement takes approximately 2 minutes, and the amount of a contrast agent contained in the object decreases remarkably in that period. Thus, a case in which the present invention is applied to such a case will be described below.

Example 1

FIG. 1 is a block diagram illustrating Example 1 of a photoacoustic apparatus according to an embodiment of the present invention. A photoacoustic apparatus 1000 (hereinafter referred to simply as an "apparatus 1000") of Example 1 basically includes a light source 11, an optical system 13, an injection unit 14, a probe (corresponding to a receiving unit) 17, a signal collecting unit 18, a signal processing unit 19, and a display unit 20. The apparatus 1000 is configured to be able to acquire object information such as an optical characteristic value inside an object as a visible image. In the following description, three light absorbers will be defined and used for description. That is, the three light absorbers are defined as a contrast agent 1012 which is an artificial light absorber, a non-artificial light absorber 1014 which is a light absorber other than the contrast agent 1012, and a combined light absorber 101 which is a combination of both absorbers.

An overall flow of the operation of the apparatus 1000 is as follows. That is, pulsed light 12 emitted from the light source 11 is guided to an object 15 (a cancer, a new-born blood vessel, the face, the skin, a living body, or the like) and radiated to the object 15 while being processed into a desired light distribution shape by the optical system 13 such as, for example, a lens, a mirror, an optical fiber, or a diffuser. The light radiated to the object 15 propagates through the inside the object 15. A portion of the energy of the propagating light is absorbed in the non-artificial light absorber (a blood vessel or the like) 1014, the contrast agent 1012, or the combined light absorber 101 made up of a segment in which both the absorber and the agent are present. Which one of the non-artificial light absorber 1014, the contrast agent 1012, and the combined light absorber 101 best absorbs the irradiation light from the light source 11 depends on the wavelength of the light. These light absorbers 1012, 1014, and 101 are thermally expanded by absorbing the energy of the light to generate acoustic waves 16. The probe 17 detects the acoustic waves. The probe 17 moves to an arbitrary reception position around the object 15. The probe 17 receives acoustic waves propagating from the object 15 irradiated with the pulsed light at the reception position to output an electrical signal as the reception result.

The injection unit 14 injects the contrast agent 1012 into the object 15. After that, the probe 17 receives photoacoustic waves at a plurality of reception positions while moving. The signal collecting unit 18 receives the electrical signals output from the probe 17 as an input signal, amplifies the input signal while performing analog/digital conversion on the input signal to form a digital signal, and outputs the digital signal to the signal processing unit 19. The signal processing unit 19 performs a predetermined process described later on the output digital signal, form image data indicating an optical characteristic value, and outputs the image data to the display unit 20. The display unit 20 is provided as a user interface and displays a visible image based on the output image data. In the following description, the "digital signal" indicates a signal generated by the signal collecting unit 18.

<<Light Source>>

When the object 15 is a living body, the light source 11 radiates light of a specific wavelength absorbed in a specific component (for example, the blood) within the living body. The light source 11 is preferably a pulsating light source capable of generating pulsed light of several nanoseconds to several hundreds of nanoseconds. The light source 11 is preferably a laser but may be configured as a light-emitting diode or the like instead of the laser. Various lasers such as a solid laser, a gas laser, a dye laser, or a semiconductor laser can be used for the light source 11. In this example, a single light source is used as the light source 11. However, the light source is not limited thereto but a plurality of light sources may be used. In this case, the light source 11 is made up of a plurality of light sources that oscillates light of the same wavelength. By doing so, the irradiation intensity of light radiated to the object 15 increases. Moreover, when the light source 11 is made up of a plurality of light sources having different oscillation wavelengths, a wavelength-dependent difference in an optical characteristics distribution can be measured. When the light source 11 is configured as a laser which uses a dye or optical parametric oscillators (OPOs) capable of variably controlling an oscillation frequency, the apparatus 1000 can measure a wavelength-dependent difference in an optical characteristics distribution. The wavelength of light generated from the light source 11 is preferably in a wavelength region of 700 nm to 1100 nm in which light is less absorbed in a living body which is the object 15. However, when it is desired to obtain an optical characteristics distribution of a living body tissue located relatively close to the surface of a living body, the wavelength of light generated from the light source 11 may be in a wavelength region of 400 nm to 1600 nm, for example, wider than the above-mentioned wavelength region. When the object 15 is a living body, in particular, the wavelength of light generated by the light source 11 is preferably in a near-infrared wavelength range of 700 nm to 900 nm in which safety is secured when the light is radiated to the living body and in which light is highly transmissive in the living body. A pulse width of the pulsed light 12 emitted from the light source 11 preferably set so as to satisfy heat and stress confining conditions in order to efficiently confine the energy absorbed in the light absorber. The pulse width of the pulsed light 12 emitted from the light source 11 is approximately between 1 nanoseconds and 200 nanoseconds, for example.

<<Optical System 13>>

The optical system 13 guides the light 12 emitted from the light source 11 to the object 15 while processing the light into a desired light distribution shape using an optical component such as a lens, a mirror, and the like. Alternatively, the optical system 13 may be configured to allow the light 12 to propagate with the aid of an optical waveguide such as an optical fiber or the like so that the light 12 is guided from the light source 11 to the object 15. The optical system 13 may include an optical component such as, for example, a mirror for reflecting light, a lens for condensing, expanding, or changing the shape of light, or a diffuser that diffuses light. However, the optical component is not limited thereto but various components capable of irradiating the light 12 emitted from the light source 11 to the object 15 in a desired shape can be used as the optical component. The light 12 may be condensed by a lens. However, the present invention is not limited thereto but the light 12 may be expanded in a certain size of area so that a diagnosis region is broadened while guaranteeing the safety of a living body.

<<Object 15>>

Although the object 15 is not a constituent element of the apparatus 1000, the object 15 will be described in this section for the sake of convenience. The apparatus 1000 is used for diagnosing blood diseases or malignant tumors of a person or an animal and observing the progress of chemical treatments, for example. Thus, the object 15 is a living body and is a segment serving as a diagnosis target such as the breast, the fingers, and the limbs of a person or an animal. In this example, the object 15 may include a light absorber which can be present inside the object 15 without being injected from the outside of the object 15 and a light absorber which can be present inside the object 15 by being injected from the outside of the object 15. Examples of the former light absorber include oxygenated hemoglobin, reduced hemoglobin, or a blood vessel including both hemoglobins, and an example of the latter light absorber is the contrast agent 1012 or the like. The object 15 injected with the contrast agent 1012 may be processed in the following manner when photoacoustic measurement is performed by the apparatus 1000. That is, an electrical signal based on acoustic waves originating from hemoglobin in a blood vessel, which is the non-artificial light absorber 1014 and an electrical signal based on acoustic waves originating from the contrast agent 1012 injected from the outside may be extracted separately. By doing so, an image originating from the hemoglobin in the blood vessel, which is the non-artificial light absorber 1014 and an image originating from the contrast agent 1012 can be formed separately based on the respective electrical signals. Alternatively, the object 15 injected with the contrast agent 1012 may be processed in the following manner during the photoacoustic measurement. That is, an electrical signal based on acoustic waves originating from hemoglobin in a blood vessel, which is the non-artificial light absorber 1014 and an electrical signal based on acoustic waves originating from the contrast agent 1012 injected from the outside may not be separated but a mixed electrical signal in which the two electrical signals are mixed is acquired. Moreover, a method of use may be acquisition of an image on the basis of the mixed electrical signal. By doing so, since the electrical signal originating from the contrast agent 1012 is combined with the electrical signal originating from the hemoglobin in the blood vessel, which is the non-artificial light absorber 1014, a display image, further enhanced for the brightness or the like of an image of a blood vessel portion in the object 15, can be acquired in proportion to a degree of signal combination.

<<Contrast Agent 1012>>

In the present specification, the contrast agent 1012 mainly indicates a light absorber injected into the object 15 from the outside of the object 15 for the purpose of improving the contrast (S/N ratio) of a photoacoustic signal distribution. However, the contrast agent 1012 may include a material that controls a movement inside the body other than a light absorber itself. Examples of the material that control a movement in the body include a serum-derived protein such as albumin or IgG and a water-soluble synthetic polymer such as polyethylene glycol. Thus, in the present specification, the contrast agent 1012 includes a light absorber itself, a material that forms a covalent bond with a light absorber, and a material in which a light absorber and another material are held by physical interaction.

When the object 15 is a living body, near-infrared light (wavelength: between 600 nm and 900 nm) is preferably used as irradiation light from the perspective of the safety and a transmissive property in a living body. Thus, a material having a light absorbing property in at least a near-infrared wavelength region is used as the contrast agent 1012. Examples of such a material include an organic compound represented by a cyanine-based compound (also referred to as a cyanine dye) represented by indocyanine green and an inorganic compound represented by gold or iron oxides.

[Chemical Formula 1]

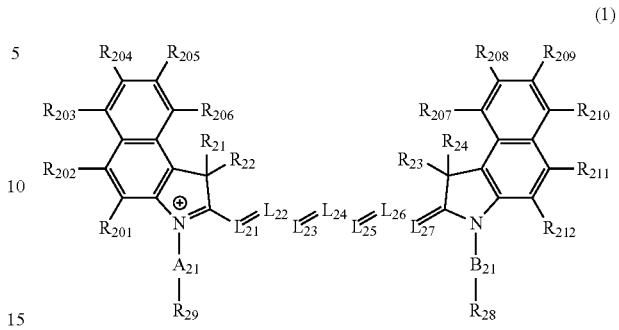

(1)

In Formula (1), $R_{201}$ to $R_{212}$ each independently represent a hydrogen atom, a halogen atom, $SO_3T_{201}$, $PO_3T_{201}$, a benzene ring, a thiophene ring, a pyridine ring, or a linear or branched alkyl group having 1 to 18 carbon atoms. $T_{201}$ represents either a hydrogen atom, a sodium atom, or a potassium atom. In Formula (1), $R_{21}$ to $R_{24}$ each independently represent a hydrogen atom or a linear or branched alkyl group having 1 to 18 carbon atoms. In Formula (1), $A_{21}$ and $B_{21}$ each independently represents a linear or branched alkylene group having 1 to 18 carbon atoms. In Formula (1), $L_{21}$ to $L_{27}$ each independently represent CH or, $CR_{25}$. $R_{25}$ represents a linear or branched alkyl group having 1 to 18 carbon atoms, a halogen atom, a benzene ring, a pyridine ring, a benzyl group, $ST_{202}$, or a linear or branched alkylene group having 1 to 18 carbon atoms. $T_{202}$ represents a linear or branched alkyl group having 1 to 18 carbon atoms, a benzene ring, or a linear or branched alkylene group having 1 to 18 carbon atoms. In Formula (1), $L_{21}$ to $L_{27}$ may form 4-membered to 6-membered rings. In Formula (1), $R_{28}$ represents either —H, —OCH$_3$, —NH$_2$, —OH, —CO$_2$T$_{28}$, —S(=O)$_2$OT$_{28}$, —P(=O) (OT$_{28}$)$_2$, —CONH—CH(CO$_2$T$_{28}$)-CH$_2$ (C=O)OT$_{28}$, —CONH—CH(CO$_2$T$_{28}$)-CH$_2$CH$_2$ (C=O)OT$_{28}$, or —OP(=O) (OT$_{28}$)$_2$. $T_{28}$ represents either a hydrogen atom, a sodium atom, or a potassium atom. In Formula (1), $R_{29}$ represents either —H, —OCH$_3$, —NH$_2$, —OH, —CO$_2$T$_{29}$, —S(=O)$_2$OT$_{29}$, —P(=O) (OT$_{29}$)$_2$, —CONH—CH(CO$_2$T$_{29}$)-CH$_2$ (C=O)OT$_{29}$, —CONH—CH(CO$_2$T$_{29}$)-CH$_2$CH$_2$ (C=O)OT$_{29}$, or —OP(=O) (OT$_{29}$)$_2$. $T_{29}$ represents either a hydrogen atom, a sodium atom, a potassium atom.

[Chemical Formula 2]

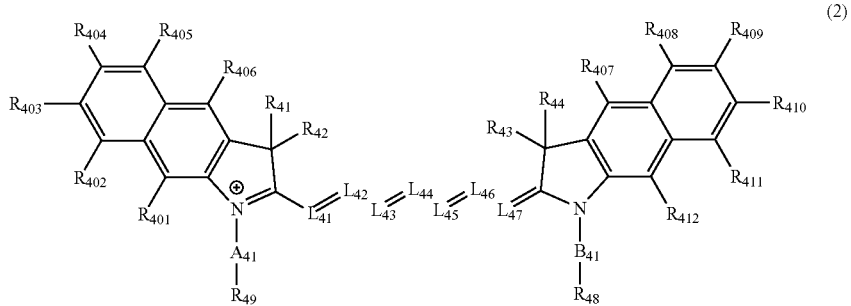

(2)

In this example, the cyanine-based compound preferably has a molar absorption coefficient of at least $10^6$ M$^{-1}$ cm$^{-1}$ in an absorption maximum wavelength. Examples of the structure of the cyanine-based compound used in this example are expressed by General Formula (1) to (4) below.

In Formula (2), $R_{401}$ to $R_{412}$ each independently represent a hydrogen atom, a halogen atom, a $SO_3T_{401}$, $PO_3T_{401}$, a benzene ring, a thiophene ring, a pyridine ring, or a linear or branched alkyl group having 1 to 18 carbon atoms. $T_{401}$ represents either a hydrogen atom, a sodium atom, or a potassium atom. In Formula (2), $R_{41}$ to $R_{44}$ each independently represent a hydrogen atom or a linear or branched alkyl group having 1 to 18 carbon atoms. In Formula (2), $A_{41}$ and $B_{41}$ each independently represent a linear or branched alkylene group having 1 to 18 carbon atoms. In Formula (2), $L_{41}$ to $L_{47}$ each independently represent CH or $CR_{45}$. $R_{45}$ represents a linear or branched alkyl group having 1 to 18 carbon atoms, a halogen atom, a benzene ring, a pyridine ring, a benzyl group, $ST_{402}$, or a linear or branched alkylene group having 1 to 18 carbon atoms. $T_{402}$ represents a linear or branched alkyl group having 1 to 18 carbon atoms, a benzene ring, or a linear or branched alkylene group having 1 to 18 carbon atoms. In Formula (2), $L_{41}$ to $L_{47}$ may form a 4-membered ring or 6-membered ring. In Formula (2), $R_{48}$ represents either —H, —OCH$_3$, —NH$_2$, —OH, —CO$_2$T$_{48}$, —S(=O)$_2$OT$_{48}$, —P(=O) (OT$_{48}$)$_2$, —CONH—CH(CO$_2$T$_{48}$)-CH$_2$ (C=O) OT$_{48}$, —CONH—CH(CO$_2$T$_{48}$)-CH$_2$CH$_2$ (C=O)OT$_{48}$, or —OP(=O) (OT$_{48}$)$_2$. $T_{48}$ represents either a hydrogen atom, sodium atom, potassium atom. In Formula (2), $R_{49}$ represents either —H, —OCH$_3$, —NH$_2$, —OH, —CO$_2$T$_{49}$, —S(=O)$_2$OT$_{49}$, —P(=O) (OT$_{49}$)$_2$, —CONH—CH(CO$_2$T$_{49}$)-CH$_2$ (C=O)OT$_{49}$, —CONH—CH(CO$_2$T$_{49}$)-CH$_2$CH$_2$ (C=O)OT$_{49}$, or —OP(=O) (OT$_{49}$)$_2$. $T_{49}$ represents either a hydrogen atom, a sodium atom, or a potassium atom.

(OT$_{69}$)$_2$, —CONH—CH(CO$_2$T$_{69}$)-CH$_2$ (C=O) OT$_{69}$, —CONH—CH(CO$_2$T$_{69}$)-CH$_2$CH$_2$ (C=O) OT$_{69}$, or —OP (=O) (OT$_{69}$)$_2$. $T_{69}$ represents either a hydrogen atom, a sodium atom, or a potassium atom.

[Chemical Formula 4]

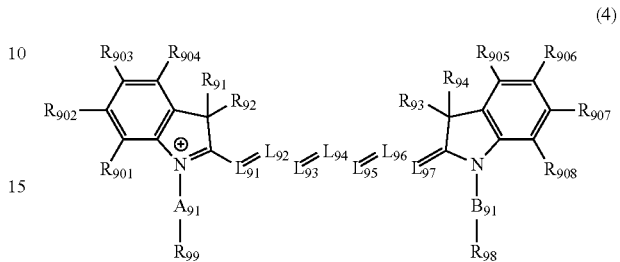

(4)

In Formula (4), $R_{901}$ to $R_{908}$ each independently represent a hydrogen atom, a halogen atom, $SO_3T_{901}$, $PO_3T_{901}$, a benzene ring, a thiophene ring, a pyridine ring, or a linear or branched alkyl group having 1 to 18 carbon atoms. $T_{901}$ represents either a hydrogen atom, a sodium atom, or a potassium atom. In Formula (4), $R_{91}$ to $R_{94}$ each independently represent a hydrogen atom or a linear or branched alkyl group having 1 to 18 carbon atoms. In Formula (4), $A_{91}$ and $B_{91}$ each independently represent a linear or branched alkylene group having 1 to 18 carbon atoms. In Formula (4), $L_{91}$ to $L_{97}$ each independently represent CH or $CR_{95}$. $R_{95}$ represents a linear or branched alkyl group having 1 to 18 carbon atoms, a halogen atom, a benzene ring, a pyridine ring, a benzyl group, $ST_{902}$, or a linear or branched alkylene group having 1 to 18 carbon atoms. $T_{902}$ represents a linear or branched alkyl group having 1 to 18 carbon atoms, a benzene ring, or a linear or branched alkylene group having 1 to 18 carbon atoms. In Formula (4), $L_{91}$ to $L_{97}$ may form a 4-membered ring or 6-membered ring. In Formula (4), $R_{98}$ represents either —H, —OCH$_3$, —NH$_2$, —OH, —CO$_2$T$_{98}$, —S(=O)$_2$OT$_{98}$, —P(=O)(OT$_{98}$)$_2$, —CONH—CH(CO$_2$T$_{98}$)-CH$_2$ (C=O) OT$_{98}$, —CONH—CH(CO$_2$T$_{98}$)-CH$_2$CH$_2$ (C=O)OT$_{98}$, or —OP(=O) (OT$_{98}$)$_2$. $T_{98}$ represents either a hydrogen atom, a sodium atom, or a potassium atom. In Formula (4), $R_{99}$ represents either —H, —OCH$_3$, —NH$_2$, —OH, —CO$_2$T$_{99}$, —S(=O)$_2$OT$_{99}$, —P(=O) (OT$_{99}$)$_2$, —CONH—CH(CO$_2$T$_{99}$)-CH$_2$ (C=O)OT$_{99}$, —CONH—CH (CO$_2$T$_{99}$)-CH$_2$CH$_2$ (C=O)OT$_{99}$, or —OP (=O) (OT$_{99}$)$_2$. $T_{99}$ represents either a hydrogen atom, a sodium atom, or a potassium atom.

In this example, examples of the cyanine-based compound include indocyanine green, SF-64 having a benzotri-

[Chemical Formula 3]

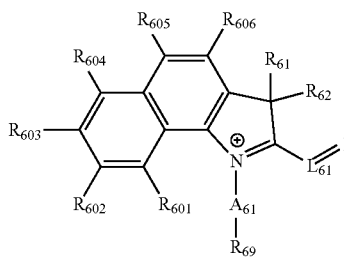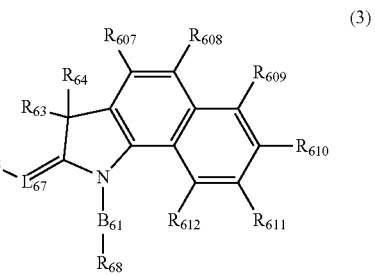

(3)

In Formula (3), $R_{601}$ to $R_{612}$ each independently represent a hydrogen atom, a halogen atom, a $SO_3T_{601}$, $PO_3T_{601}$, a benzene ring, a thiophene ring, a pyridine ring, or a linear or branched alkyl group having 1 to 18 carbon atoms. $T_{601}$ represents either a hydrogen atom, a sodium atom, or a potassium atom. In Formula (3), $R_{61}$ to $R_{64}$ each independently represent a hydrogen atom or a linear or branched alkyl group having 1 to 18 carbon atoms. In Formula (3), $A_{61}$ and $B_{61}$ represents a linear or branched alkylene group having 1 to 18 carbon atoms. In Formula (3), $L_{61}$ and $L_{67}$ each independently represent CH or, $CR_{65}$. $R_{65}$ represents a linear or branched alkyl group having 1 to 18 carbon atoms, a halogen atom, a benzene ring, a pyridine ring, a benzyl group, $ST_{602}$, or a linear or branched alkylene group having 1 to 18 carbon atoms. $T_{602}$ represents a linear or branched alkyl group having 1 to 18 carbon atoms, a benzene ring, or a linear or branched alkylene group having 1 to 18 carbon atoms. In Formula (3), $L_{61}$ to $L_{67}$ may form a 4-membered ring or 6-membered ring. In Formula (3), $R_{68}$ represents either —H, —OCH$_3$, —NH$_2$, —OH, —CO$_2$T$_{68}$, —S(=O)$_2$OT$_{68}$, —P(=O) (OT$_{68}$)$_2$, —CONH—CH(CO$_2$T$_{68}$)-CH$_2$ (C=O)OT$_{68}$, —CONH—CH(CO$_2$T$_{68}$)-CH$_2$CH$_2$ (C=O) OT$_{68}$, or —OP(=O) (OT$_{68}$)$_2$. $T_{68}$ represents either a hydrogen atom, a sodium atom, or a potassium atom. In Formula (3), $R_{69}$ represents either —H, —OCH$_3$, —NH$_2$, —OH, —CO$_2$T$_{69}$, —S(=O)$_2$OT$_{69}$, —P(=O)

carbocyanine structure expressed by Chemical Formula (1), and compounds expressed by Chemical Formula (i) to (v).

[Chemical Formula 5]

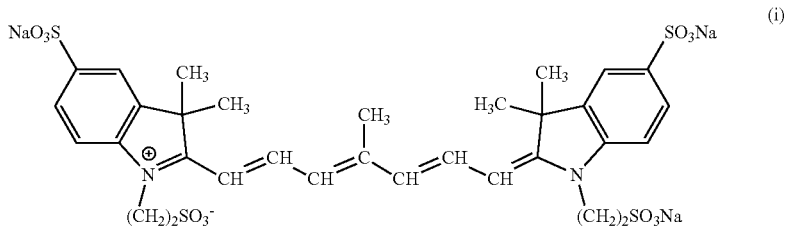

(i)

[Chemical Formula 6]

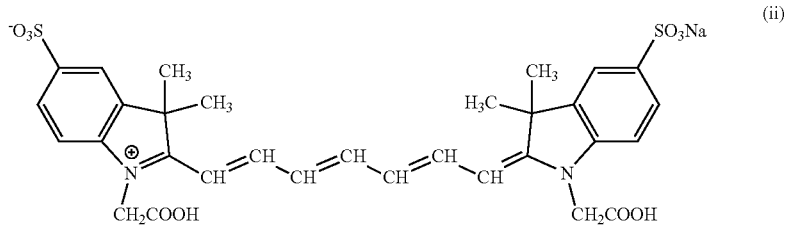

(ii)

[Chemical Formula 7]

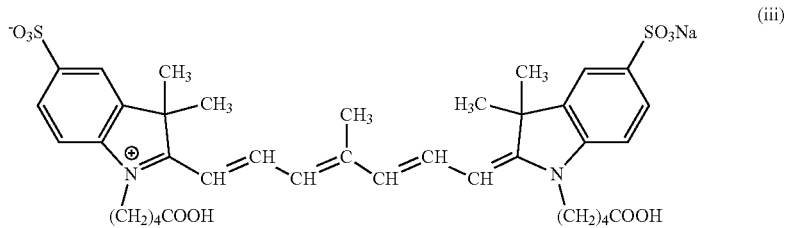

(iii)

[Chemical Formula 8]

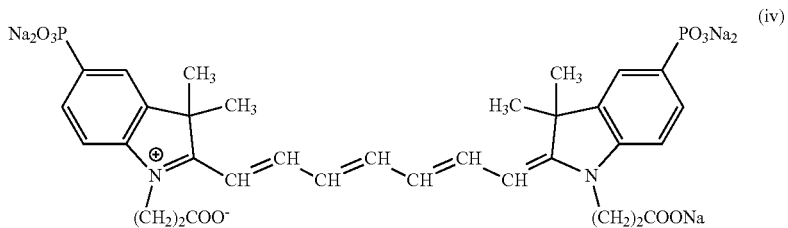

(iv)

[Chemical Formula 9]

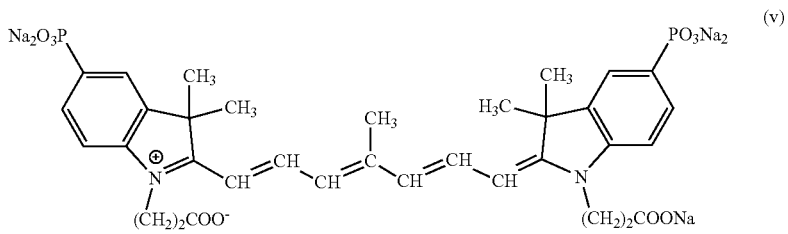

(v)

The cyanine-based compound may have an aromatic ring which is replaced with a sulfonic acid group, a carboxyl group, or a phosphate group. Moreover, a sulfonic acid group, a carboxyl group, or a phosphate group may be introduced to a portion other than the aromatic ring.

<<Injection Unit 14>>

The injection unit 14 is configured to be able to inject the contrast agent 1012 into the object 15 from the outside of the object 15. The injection unit 14 injects the contrast agent 1012 into the object 15 and outputs an injection completion signal to the signal processing unit 19 when the injection is completed. The injection completion signal is used for processing an electrical signal originating from acoustic waves. The injection unit 14 injects the contrast agent 1012 from a vein of the object 15. However, the injection unit 14 is not limited thereto but various units capable of injecting the contrast agent 1012 and transmitting the time of completion of the injection to the signal processing unit 19 can be used. In this case, the injection unit 14 may be an existing injection system, an injector, or the like, for example.

<<Probe 17>>

The probe 17 is configured to receive acoustic waves generated when pulsed light is radiated to the object 15, convert the acoustic waves to an analog electrical signal, and transmit the electrical signal to the signal collecting unit 18. The probe 17 may be configured by arranging a plurality of acoustic wave detection elements capable of receiving acoustic waves. The acoustic wave detection element may be an arbitrary element as long as it can detect acoustic waves such as an element which uses a piezoelectric phenomenon (for example, a piezoelectric element), an element which uses resonance of light, or an element which uses a change in capacitance. The probe 17 may be configured by arranging a plurality of acoustic wave detection elements in one dimension or two dimensions. When the probe 17 is configured as a multi-dimensional array of acoustic wave detection elements, the probe 17 can detect acoustic waves at a plurality of locations where the acoustic wave detection elements are present at an acoustic wave reception position of one probe 17. Thus, it is possible to shorten the acoustic wave reception time of the probe and reduce the influence on the acoustic wave detection accuracy, of vibration of the object 15. The probe 17 is configured to be movable in relation to the object 15. By doing so, the probe 17 can secure a sufficient acquisition amount of acoustic waves usable for image reconstruction. In this case, it is ideal for the probe 17 to receive acoustic waves from as many directions as possible in relation to the surface of the object 15. Thus, the probe 17 is preferably configured to be movable with the aid of a position controller 32 and be movable as wide as possible along the surface of the object 15. The position controller 32 may be a step motor capable of moving the probe 17 to an arbitrary position. The position controller 32 may move the probe around the object 15. By doing so, sufficient information for obtaining a spatial arrangement (one of items of object information) of a sound source (light absorber) in the object 15 can be acquired.

The probe 17 is configured by arranging 128 acoustic wave detection elements, for example, and the followings can be said when acoustic waves are received at 120 reception positions around the object 15. That is, the probe 17 receives acoustic waves from the object 15 with the aid of acoustic wave detection elements present at 15360 positions in total. The probe 17 is not limited thereto but the probe 17 may be configured by arranging a plurality of acoustic wave detection elements at different positions along an approximately hemispherical shape. In this case, the directions in which the reception sensitivities of the acoustic wave detection elements are highest may concentrate on a certain area located at and around the center of curvature of the approximately hemispherical shape. Moreover, the probe may be configured to be integrated with the irradiation unit 30. That is, in the case of FIG. 1, the irradiation unit 30 is provided on the front surface side of the object 15 and the probe 17 is provided on the rear surface side of the object 15. In contrast, in the case, which will be described in Example 7, the probe 17 and the irradiation unit 30 may be provided on the rear surface side of the object 15. By doing so, since light can be radiated and acoustic waves can be received while moving the probe 17 in a spiral form, it is possible to suppress noise in the received acoustic waves. The noise in acoustic waves is a wave component other than acoustic waves originating from light absorbers in the object 15. Although the probe 17 is moved in the above description, the probe 17 is not limited thereto but it is sufficient that light irradiation and reception of acoustic waves are performed while changing a positional relation between the object 15 and the probe 17. Thus, the object 15 only may be moved without moving the probe 17 and both the object 15 and the probe 17 may be moved. Moreover, the positional relation between the irradiation unit 30 and the object 15 may be changed or may be fixed. The irradiation unit 30 is configured to appropriately expand the light 12 from the light source 11 with the aid of a lens or the like (not illustrated) to form irradiation light 34 and radiate the irradiation light 34 to the object 15.

<<Signal Collecting Unit 18>

The signal collecting unit 18 receives the electrical signals output from the probe 17 as an input signal, performs analog/digital conversion on the input signal while amplifying the input signal to generate a digital signal, and outputs the digital signal to the signal processing unit 19. The signal collecting unit 18 is configured to include an amplifier (an operational amplifier or the like), an analog/digital converter, a field programmable gate array (FPGA) chip, and the like, for example. When the electrical signals output from the probe 17 are input in parallel for the respective acoustic wave detection elements, the signal collecting unit 18 is preferably configured to be able to execute processing on each electrical signal in parallel. By doing so, the time to image reconstruction can be shortened.

<<Signal Processing Unit 19>>

The signal processing unit 19 is configured to include a signal processing module (corresponding to a correction processing unit) 19a and an image reconstruction module (corresponding to an acquiring unit) 19b. The signal processing module 19a is configured to correct the digital signal using temporal change information on the blood concentration of the contrast agent 1012. The image reconstruction module 19b performs an image reconstruction process on the correction digital signal (corresponding to a corrected electrical signal) configured by performing the correction process. By doing so, image data which is one of items of characteristics information on the inside of the object 15 is formed. The signal processing unit 19 may be configured as a workstation or the like which includes a processor and a memory, for example, and the workstation may have the functions of the signal processing module 19a and the image reconstruction module 19b. The workstation performs a correction process on the digital signal acquired from the object 15 with the aid of software programmed in advance.

The signal processing module 19a is interlocked with the injection unit 14 and is configured to be able to temporally synchronize the injection operation of the contrast agent 1012, the acquisition of acoustic waves, and a temporal change in the blood concentration of the contrast agent 1012. The signal processing module 19a may perform a noise reduction process on the digital signal received from the signal collecting unit 18 and then output the digital signal to the image reconstruction module 19b. By doing so, the image reconstruction module 19b improves the S/N ratio of the acquired object information.

The image reconstruction module 19b performs an image reconstruction process on the correction digital signal output from the signal processing module 19a to form image data and outputs the image data to the display unit 20. The image reconstruction module 19b performs image reconstruction using back-projection or the like in a time or Fourier domain used in tomography techniques, for example. However, the image reconstruction module 19b is not limited thereto but the image reconstruction module 19b may perform image reconstruction using iterative inverse problem analysis or the like based on repetitive processing when a sufficient image reconstruction time can be secured. A representative example of an image reconstruction method used in the image reconstruction module 19b includes a Fourier transform method, a universal back-projection method, and a filtered back-projection method. When the probe 17 is configured as a focusing-type probe, the signal processing unit 19 can directly form image data of an optical characteristics distribution in the object 15 without performing the image reconstruction process. Moreover, the signal processing unit 19 may be configured to be integrated with the signal collecting unit 18. The device configured by the integration may generate image data based on the object 15 by performing such a software process as performed by the workstation and may generate image data based on the object 15 by performing a hardware process.

<<Display Unit 20>>

The display unit 20 is configured to receive image data output from the signal processing unit 19 and display an image visible to a user based on the input data. The display unit 20 is configured as a liquid crystal display or the like, for example. The display unit 20 may form a portion of the apparatus 1000 and may be configured to be externally attached as a separate unit from the apparatus 1000.

(Acquisition of Temporal Change Information on Contrast Agent Concentration in Blood)

Figure 2:
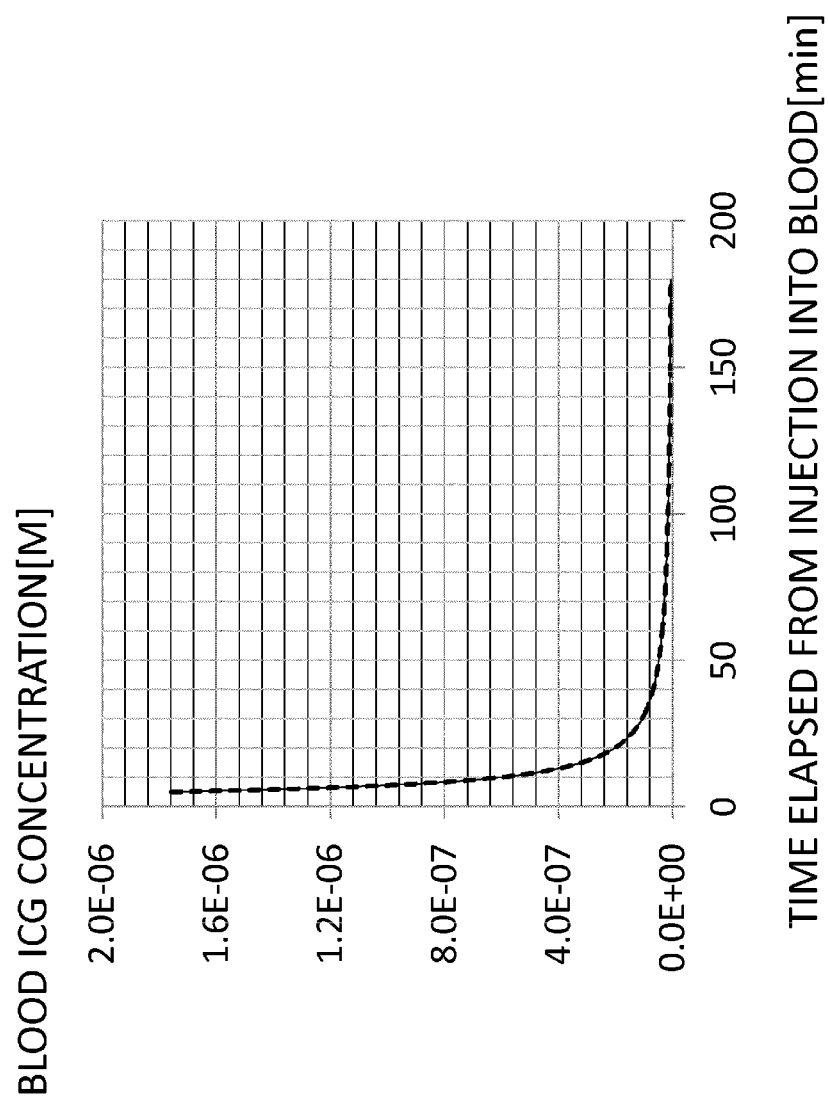
FIG. 2 is a diagram illustrating a temporal change in a contrast agent concentration in the blood when injected into a tail vein.

FIG. 2 is a diagram illustrating a temporal change in the concentration of the contrast agent 1012 in the blood when ICG (20 nanomoles) which is the contrast agent 1012 was injected into a tail vein of a nude mouse. The vertical axis of FIG. 2 represents the blood ICG concentration and the horizontal axis represents the time elapsed after the contrast agent 1012 was injected to the nude mouse. As obvious from FIG. 2, the concentration of ICG present in the blood decreases to a half or smaller within 10 minutes after injection. Acoustic waves originating from the contrast agent 1012, generated from a circulating blood portion decrease to a half or smaller within 10 minutes after injection when the generation principle of photoacoustic waves defined in Equation A is taken into consideration.

The signal processing module 19a corrects the digital signal formed based on the acoustic waves that the probe 17 receives from the object 15 based on the information on the time at which the probe 17 received the acoustic waves and the lookup table. In this way, it is possible to suppress an adverse effect on image data, of a strength variation in the acoustic waves resulting from a time lag occurring when acoustic waves are acquired. When the correction process is performed, the signal processing module 19a takes temporal synchronization between the temporal change information (the lookup table) on the concentration of the contrast agent 1012 in the blood and the acoustic wave acquisition time in the probe 17. This synchronization process will be described later. The time lag upon acquisition of acoustic waves may be defined by a period between the completion time of injection of the contrast agent 1012 into the object 15 and the reception time at which the probe 17 received the acoustic waves, for example. The signal processing module 19a is configured to read an estimated contrast agent concentration from the data in the lookup table by referring to the reception time. The lookup table is data related to a temporal change in the contrast agent concentration.

The change in the concentration of the contrast agent 1012 resulting from the time lag occurring upon acquisition of acoustic waves causes a decrease in the strength of acoustic waves acquired by the probe 17. The signal processing module 19a corrects the amount of decrease in strength by amplifying the strength of the digital signal from the signal collecting unit 18. In this case, the signal processing module 19a may include a device that acquires the temporal change information on the concentration of the contrast agent 1012 in a circulating blood, a memory that stores in advance the temporal change information on the concentration of the contrast agent 1012, or the like. When the signal processing module 19a acquires information on the temporal change of the concentration of the contrast agent 1012 in the blood, the quantity of the contrast agent 1012 in the blood is measured in a previous stage. In this case, the signal processing module 19a may measure the quantity of the contrast agent 1012 by an optical method such as a photoacoustic method, a fluorescent method, or an absorption method and may use an existing method which uses a radioisotope or the like. The signal processing module 19a stores the acquisition time of acoustic waves from the object 15 based on the time of completion of injection of the contrast agent 1012 and the concentration of the contrast agent 1012 at the acquisition time in a memory and the like (not illustrated) in correlation. By doing so, the signal processing module 19a can correct the digital signal received from the signal collecting unit 18 using a relative abundance (a relative value) in the blood of the contrast agent 1012 at the acquisition time of acoustic waves serving as the source of digital signal formation. In this way, the influence of the strength variation in acoustic waves resulting from a temporal change in the concentration of the contrast agent 1012 in the circulating blood based on the time lag occurring during acquisition of acoustic waves can be reduced. However, the present invention is not limited thereto, and a reference time—the acquisition time of the acoustic waves from the object 15—may be the first acoustic wave reception time.

When the signal processing module 19a stores the temporal change information on the concentration of the contrast agent 1012 in the circulating blood in advance, the temporal change information on the concentration of the contrast agent 1012 in the circulating blood may be various items of information from which a difference in the blood concentration at respective time points at which acoustic waves are acquired can be known. The following information may be used as the temporal change information on the concentration (corresponding to an estimated concentration) of the contrast agent 1012 in the circulating blood stored in advance. That is, the temporal change information may be saved in a lookup table saving data obtained through following procedures, in which the contrast agent 1012 is injected into the object 15 over time and the blood is collected at respective time points, and values of the concentrations of the contrast agent 1012 contained in the circulating blood at the respective collection time points are recorded. In the following description, for the sake of convenience, the temporal change information itself on the concentration of the contrast agent 1012 in the blood will be appropriately referred to as a lookup table.

(Object Information Acquisition Method)

Figure 3:
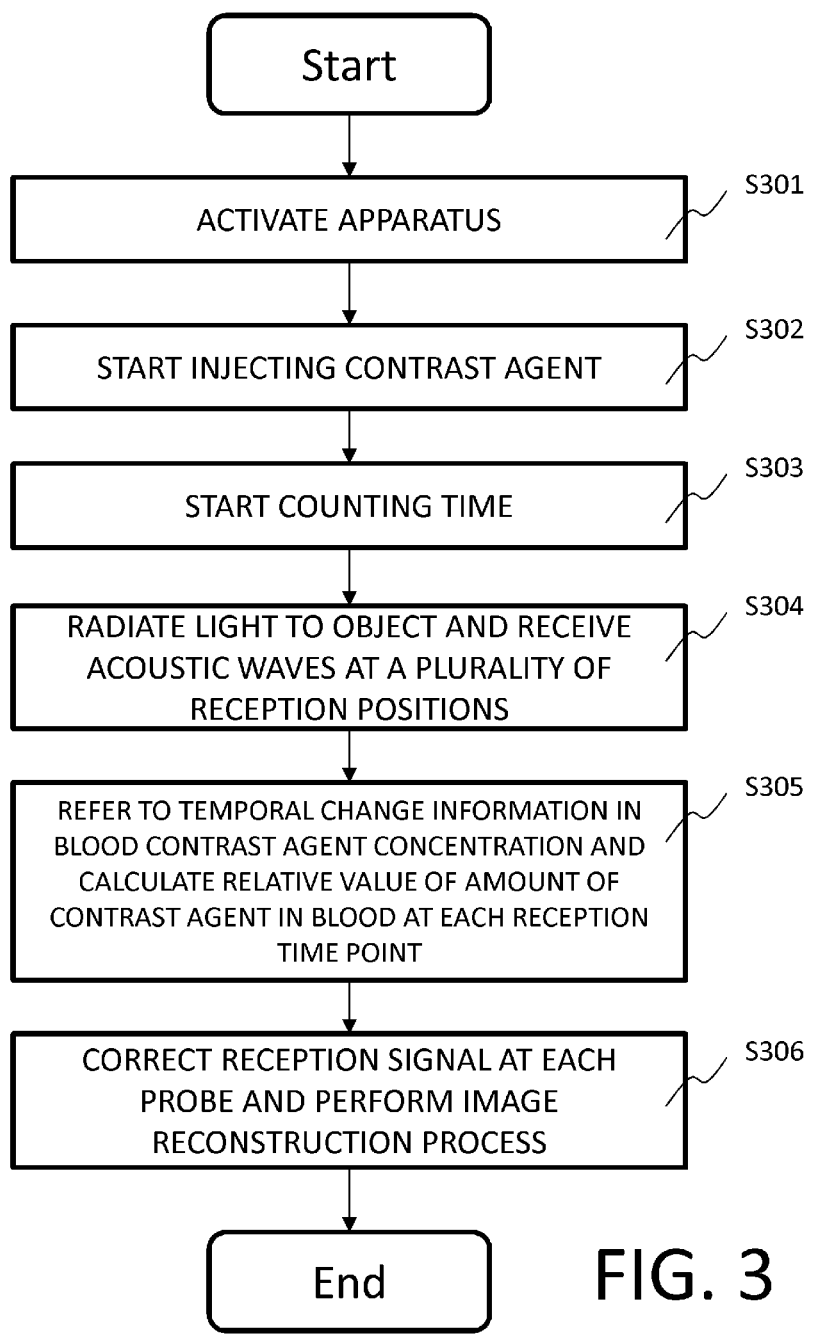
FIG. 3 is a flowchart illustrating the function of an apparatus 1000 of Example 1 of the present invention.

FIG. 3 is a flowchart illustrating the function of the apparatus 1000 according to Example 1 of the present invention. The flow starts when the object 15 is supported by a supporting portion or the like included in the apparatus 1000. When the flow starts, supply of power to the apparatus 1000 in a state in which the object 15 is supported starts and the apparatus 1000 is activated in step S301, and the flow proceeds to step S302. In step S302, the contrast agent 1012 is injected from the injection unit 14 into the object 15 and the flow proceeds to step S303. In this case, bolus infusion or the like, for example, is used as a method of injecting the contrast agent 1012.

In step S303, the counting of the time elapsed from the injection time of the contrast agent 1012 starts and the flow proceeds to step S304. This counting may be performed by a counter circuit or a time circuit which is not illustrated.

With this counting, the period elapsed after injection of the contrast agent 1012 on the lookup table (which can be called an acquisition time of each acoustic wave on the lookup table) is synchronized with an actual acquisition time of acoustic waves. When these items of time information are synchronized, the acoustic waves received from the object 15 can be corrected by the temporal change information on the concentration of the contrast agent 1012 in the blood. As a method of implementing this synchronization, an injection system generally used in an X-ray angiography system or the like can be used, for example. In this case, an injection completion signal is output to the signal processing unit 19 at the time at which injection of the contrast agent 1012 by the injection system is completed. Moreover, when an injection completion signal is input to the signal processing unit 19, the counting of time starts immediately. In this way, the period elapsed after injection of the contrast agent 1012 on the lookup table is synchronized with the time at which acoustic waves are actually acquired by measurement.

In step S304, light is radiated to the object and acoustic waves based on the irradiation are received at a plurality of acoustic wave reception positions, and the flow proceeds to step S305. In this case, the probe 17 moves around the object 15 while light is sequentially radiated by the irradiation unit 30, whereby acoustic waves are received sequentially. In this case, the probe 17 is moved so as to pass through predetermined reception positions and acoustic waves are received at the respective predetermined reception positions. In this case, before the probe 17 is moved, the setting values of the predetermined reception positions may be input to the display unit 20 by a user so that the predetermined reception positions are set in advance. The reception time of acoustic waves at each reception position and the digital signal based on the acoustic wave at that time are stored in the signal processing unit 19 in one-to-one correlation.

When the object 15 is a living body, the received acoustic waves include acoustic waves originating from the non-artificial light absorber 1014 such as hemoglobin. Here, the following cases may occur. That is, only the electrical signal originating from the acoustic waves of the contrast agent 1012 injected into the object 15 is acquired. Subsequently, only the electrical signal originating from acoustic waves of the non-artificial light absorber 1014 is acquired. Moreover, the signals based on the acoustic waves originating from the contrast agent 1012 and the non-artificial light absorber 1014, respectively, are corrected separately. In this case, the signals may be processed in the following manner. That is, in step S304, light having a wavelength absorbed mainly by the non-artificial light absorber 1014 is radiated to the object 15 and acoustic waves generated based on the irradiation are received. When the receiving operation ends, light having a wavelength mainly absorbed by the contrast agent 1012 is subsequently radiated to the object 15 and acoustic waves generated based on the irradiation are received. In this case, the same effect as a case of irradiating light having a single wavelength except that the wavelengths of light radiated are used separately is obtained.

However, the present invention is not limited thereto, but light may be radiated to the object 15 in which the contrast agent 1012 is not contained and acoustic waves based on the irradiation may be received in a stage before the contrast agent 1012 is injected in step S302, for example. Moreover, the signal collecting unit 18 may generate a digital signal based on the acoustic waves. The digital signal may be stored in the signal processing unit 19 in correlation with the reception time of the acoustic waves serving as the source of the digital signal. In step S304, light of a single wavelength is radiated to the object 15 in which the contrast agent 1012 is contained. The acoustic waves generated based on the irradiation are received to form a digital signal, and a difference between the formed digital signal and the stored digital signal is acquired by the signal processing unit 19. By doing so, the difference is substantially a digital signal originating from the contrast agent 1012, and the digital signal originating from the contrast agent 1012 is separated and acquired.

In step S305, a relative value of the abundance of the contrast agent 1012 in the blood at each reception time is calculated by referring to the temporal change information (the lookup table) on the concentration of the contrast agent 1012 present in the blood, and the flow proceeds to step S306. In this case, in step S305, the acoustic wave reception time at each reception position stored in the signal processing unit 19 is referred to. The concentration information of the contrast agent 1012 at the referred acoustic wave reception time is referred to among the items of temporal change information on the concentration of the contrast agent 1012. In this way, the concentration of the contrast agent 1012 present in the blood in the object 15 at the reference time is acquired. Moreover, the acquired concentration of the contrast agent 1012 present in the blood in the object 15 at the reference time is divided by the concentration of the contrast agent 1012 in the blood at the first acoustic wave reception time. By doing so, the ratio (the relative value) of the concentration of the contrast agent 1012 in the blood in the object 15 at the reference time is calculated. When the relative value is calculated for all reception time points during the actual measurement, the relative value is calculated for each of the concentrations of the contrast agent 1012 at all reception time points during the actual measurement. In this case, the concentration of the contrast agent 1012 in the blood at the first acoustic wave reception time is acquired in a stage before the dividing process is performed. In this case, the concentration of the contrast agent 1012 in the blood at the first reception time may also be acquired by referring to the temporal change information on the concentration of the contrast agent 1012. However, the present invention is not limited thereto, but the acquired concentration of the contrast agent 1012 present in the blood in the object 15 at the reference time may be divided by the concentration of the contrast agent 1012 in the blood at the time of completion of the injection of the contrast agent 1012.

The relative value is used as a conversion coefficient when the digital signal formed from acoustic waves is corrected, which will be described later. Moreover, the number of relative values that are to be acquired may be input via the display unit 20 by the user in a stage before the relative value is calculated, and a number of relative values corresponding to the input number may be calculated. By doing so, the relative values at representative reception positions only are calculated and the calculation time can be shortened. In this case, the reception position or the reception time corresponding to the relative value that is to be acquired may be set via the display unit 20 by the user. Moreover, the relative value to be acquired may be automatically determined based on the setting, and the determined relative value may be calculated automatically.

In step S304, as an example, the probe 17 is moved to predetermined 120 reception positions in one photoacoustic measurement and acoustic waves are received at each reception position. In step S306 described later, the following process is performed when a decrease in the concentration of the contrast agent 1012 in the blood is corrected once at each reception position. That is, in step S305, 120 relative values are calculated based on the temporal change information on the concentration of the contrast agent 1012 in the blood, which has been acquired and stored in advance. Alternatively, in step S304, as another example, pulsed laser light 12 may be radiated a plurality of number of times at the same reception position, and acoustic waves generated based on the irradiation may be received, and an electrical signal based on the acoustic waves may be averaged. In this case, a correction process on the subsequent stage may be performed in each irradiation of the pulsed laser light 12. Moreover, in step S305, as still another example, a threshold is provided at which it can be determined that a temporal change in the concentration of the contrast agent 1012 in the blood between two or more different reception positions is substantially negligible. The same relative value may be allocated to digital signals based on the acoustic waves received at two or more reception positions in which a concentration change of the threshold or smaller occurs. In step S306 described later, the digital signals at the reception positions in which the concentration change of the threshold or smaller occurs may be corrected using the same relative value. By doing so, the number of relative values calculated decreases and the computation time of the apparatus 1000 can be reduced. The light 12 used in each of the steps may be pulsed laser light having a single wavelength. The light source 11 may be a wavelength-variable laser capable of emitting light of a plurality of wavelengths in a switching manner, and the light 12 in each of the steps may be pulsed laser light having a plurality of wavelengths.

In step S306, the digital signal from the signal collecting unit 18 is corrected to form a correction digital signal, an image reconstruction process is performed on the correction digital signal to form image data, and the flow ends. In this case, in step S306, the digital signal based on acoustic waves acquired at the reception position (or the reception time) is corrected based on the reception position (or the reception time) and the relative value correlated thereto. A correction digital signal obtained as the result of the correction process is stored in a memory or the like (not illustrated) in the signal processing unit 19. After the correction digital signals at all reception positions are stored, an image reconstruction process is performed on the stored correction digital signals to form image data. The image data is 3-dimensional voxel data. However, the image data is not limited thereto but the image data may be 2-dimensional or 1-dimensional data. Further, these items of 1-, 2-, or 3-dimensional data may be selected appropriately via the display unit 20 by the user and the image data of the selected dimension may be formed.

In the image data formed in this manner, a decrease in the accuracy of a brightness value or the like of the image data due to a decrease in the concentration of the contrast agent 1012 present in the blood, resulting from a time lag occurring during photoacoustic measurement, is suppressed. In step S306, the reciprocal of the relative value calculated in the process of step S305 is calculated at each reception position and is stored in a memory or the like (not illustrated) in the signal processing unit 19 in correlation with the reception position or the reception time. Each of the stored reciprocals is a conversion coefficient used in a subsequent correction process. The digital signal formed from acoustic waves originating from the contrast agent 1012, received at a certain reception position is multiplied with a conversion coefficient corresponding to the reception position, whereby a digital signal based on the acoustic waves received at the reception position is corrected and a correction digital signal is generated. In this case, the correction process is executed on the digital signals at all reception time points, whereby the correction digital signals are generated for all digital signals. The correction digital signal generated at each reception position is stored in a memory or the like (not illustrated) in the signal processing unit 19. In this example, it is assumed that each reception position corresponds to each acoustic wave reception time in one-to-one correlation.

As another example of the correction method, in step S305, the ratio of the concentration of the contrast agent 1012 in the blood at reception positions to the concentration of the contrast agent 1012 in the blood at the last reception position is calculated. The calculation result is stored as a relative value, and in step S306, the digital signal based on the corresponding reception position is corrected similarly by multiplying the relative value with the digital signal. However, the present invention is not limited thereto, but the conversion coefficient may be set so as to average the digital signal based on the acoustic waves obtained from the average concentration of the contrast agent 1012 in the blood during photoacoustic measurement.

In step S306, the stored correction digital signal is read and an image reconstruction process is performed on the correction digital signal to generate image data. In this case, an image reconstruction process may be performed on each correction digital data corresponding to each reception position to generate image data which is 3-dimensional voxel data. Alternatively, all correction digital signals may be divided into a plurality of groups, and image reconstruction may be performed on each group to generate image data which is 3-dimensional voxel data of each group. In this case, in step S306, the image reconstruction process is performed according to a Fourier transform method, a universal back-projection method, a filtered back-projection method, or a sequential reconstruction method. However, the present invention is not limited thereto but various image reconstruction methods may be used.

Therefore, the following effects are obtained under such photoacoustic measurement conditions that, since the contrast agent 1012 injected into the object 15 (in particular, a living body) has a short half-life in the blood, it is difficult to stably obtain acoustic waves generated from the contrast agent 1012 without a variation. That is, with the above-described processes, it is possible to form a display image and image data which is object information in which the influence of a strength variation in acoustic waves resulting from a measurement period is suppressed.

A photoacoustic apparatus according to an embodiment of the present invention can be read a photoacoustic apparatus including: a light source configured to irradiate light to an object that contains a contrast agent; an acoustic wave receiving unit configured to receive acoustic waves generated when the contrast agent absorbs the light radiated by the light source to output an electrical signal; a correction processing unit configured to correct a signal strength of the electrical signal based on information on a temporal change in a concentration of the contrast agent contained in the object; and an information acquiring unit configured to acquire characteristics information of the object based on the electrical signal corrected by the correction processing unit.

Example 2

Figure 4:
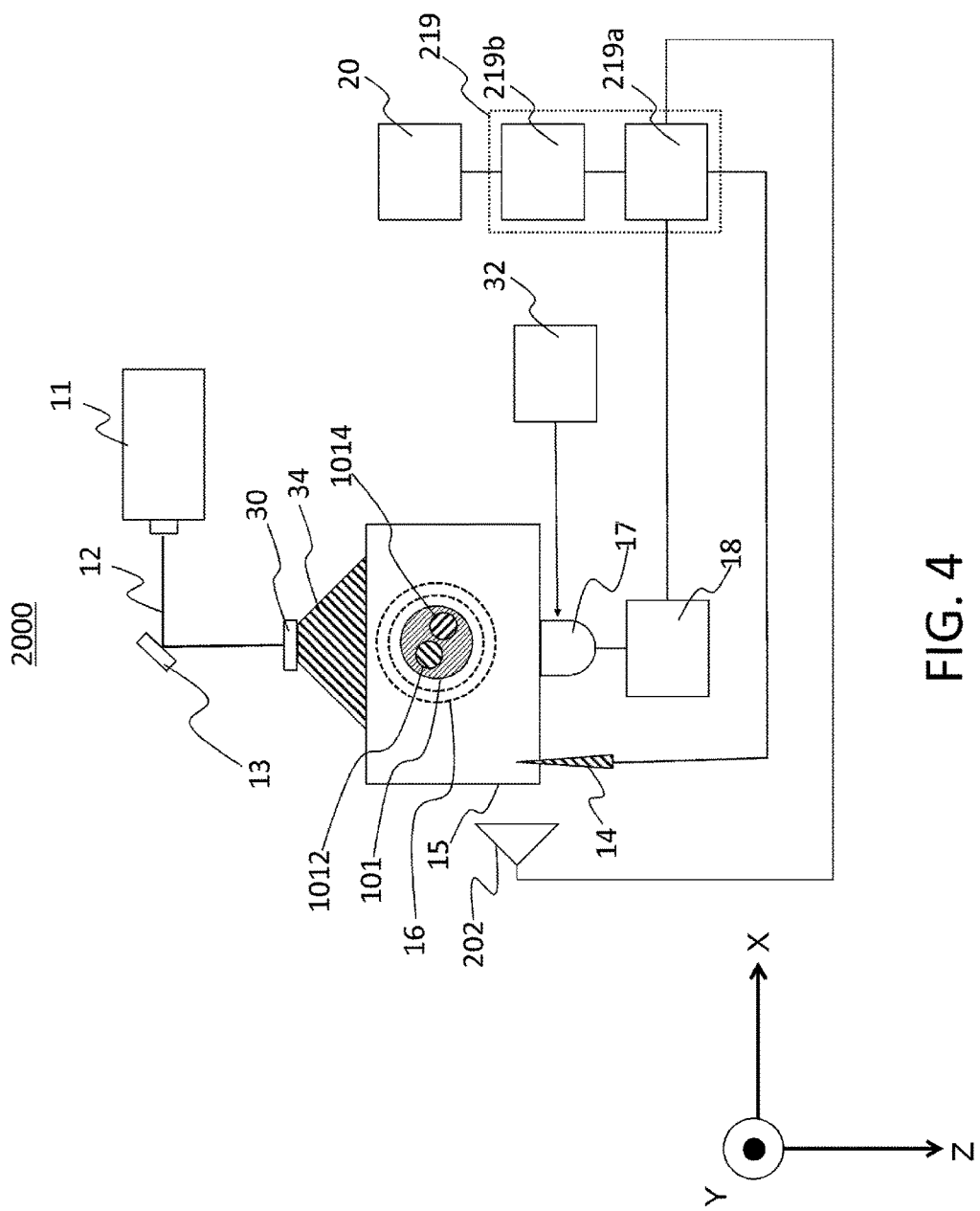
FIG. 4 is a block diagram illustrating Example 2 of the photoacoustic apparatus of the present invention.

FIG. 4 is a block diagram illustrating Example 2 of the photoacoustic apparatus according to the embodiment of the present invention, in which the same constituent elements as those of Example 1 will be denoted by the same reference numerals and the description thereof will not be provided.

Moreover, constituent elements similar to those of Example 1 will be denoted by reference numerals 2xy, in which common numbers are assigned to the ten's digit number (x) and the one's digit number (y) and the description thereof will not be provided unless necessary. A photoacoustic apparatus 2000 (hereinafter referred to simply as an "apparatus 2000") of this example is configured to be able to start counting the reception time based on a detection signal which is based on the injection completion time of the contrast agent 1012 in order to refer to a lookup table. By doing so, the apparatus 2000 can refer to the lookup table and correct the digital signal by synchronizing the lookup table with the actual acoustic wave reception time. In this example, the counting of the reception time starts based on a detection signal instead of the injection completion signal output by the injection unit 14 in Example 1.

A contrast agent detection unit 202 is configured to be able to transmit and receive signals to and from a signal processing module 219a and receives a signal from the contrast agent 1012, the signal capable of specifying the presence of the contrast agent 1012. By doing so, it is detected that the contrast agent 1012 is injected reliably into the blood, and a detection signal which is a detection result thereof is output to the signal processing module 219a. The signal processing module 219a receives the output detection signal and executes a correction process using the reception time as a reference time of the lookup table. The method in which the contrast agent detection unit 202 detects the contrast agent 1012 is not limited to an optical method such as a photoacoustic method, a fluorescent method, or an absorption method but the presence of the contrast agent 1012 may be detected using an existing method such as a method of detecting a radioisotope. Moreover, although the contrast agent detection unit 202 detects the presence of the contrast agent 1012 by receiving acoustic waves originating from the contrast agent 1012, the present invention is not limited thereto but various signals capable of specifying the presence of the contrast agent 1012 may be used. The contrast agent detection unit 202 may be provided near the distal end of the injection unit 14. This is because the contrast agent 1012 is injected from the injection unit 14 and signals originating from the contrast agent 1012 can be received easily. Alternatively, the contrast agent detection unit 202 may be provided in a position other than the position near the distal end of the injection unit 14. For example, when the contrast agent 1012 is injected from a vein, the contrast agent detection unit 202 is provided in a carotid portion and acquires a signal (a photoacoustic wave or the like) capable of specifying the presence of the contrast agent 1012 immediately after the contrast agent 1012 is injected into the carotid portion. The contrast agent detection unit 202 outputs a detection signal to the signal processing unit 219 as the acquisition result. The signal processing module 219a starts counting time immediately based on the input of the detection signal. By doing so, the signal processing module 219a synchronizes the period elapsed after injection of the contrast agent 1012 on the lookup table (the reception time of each acoustic wave on the lookup table) with the actual acoustic wave reception time. By doing so, the signal processing module 219a can refer to the lookup table when correcting the digital signal.

The present invention is not limited thereto, but the contrast agent detection unit 202 may detect the absence of the contrast agent 1012 and output a detection signal which is a detection result thereof to the signal processing module 219a. The signal processing module 219a may cause the injection unit 14 to inject the contrast agent 1012 based on the output detection signal. After that, similarly to Example 1, a detection signal is output to the signal processing unit 219 at the time at which injection of the contrast agent 1012 by the injection unit 14 which is an injection system is completed. Moreover, when a detection signal is input to the signal processing unit 219, the counting of time starts immediately. In this way, the period elapsed after injection of the contrast agent 1012 on the lookup table (the acoustic wave reception time on the lookup table) may be synchronized with the actual acoustic wave acquisition time.

<Modification of Apparatus 2000>

A modification of the apparatus 2000 will be described. In the photoacoustic apparatus according to this modification, the contrast agent detection unit 202 has a threshold set therein and is configured to output a detection signal to the signal processing module 219a only when a signal indicating the presence of the contrast agent 1012 generated from the contrast agent 1012 exceeds the threshold. Here, the contrast agent detection unit 202 of Example 2 is provided to check the completion of injection of the contrast agent 1012. Here, when a sufficient initial concentration of the contrast agent 1012 in the circulating blood is not obtained due to faulty operation of injecting the contrast agent 1012 by the injection unit 14, the acoustic wave reception result may not reflect the lookup table sufficiently. In this case, the signal processing module 219a may be unable to execute correction properly. Thus, by providing the threshold, the signal processing module 219a can determine whether correction can be performed using the lookup table. Alternatively, as another method, various patterns of the temporal change in the blood concentration of the contrast agent 1012 corresponding to various initial concentrations of the contrast agent 1012 injected into the blood of the object 15 may be predicted. In this case, lookup tables of various initial concentrations and the thresholds corresponding thereto are set in advance. Moreover, a corresponding appropriate lookup table may be selected according to a signal strength of signals received by the contrast agent detection unit 202 and the digital signal may be corrected using the selected lookup table.

Example 3

A photoacoustic apparatus according to this example is configured to be able to set an interest area for performing a correction process on a digital signal in addition to the basic function of the photoacoustic apparatus of Example 1 or 2. The apparatus of Example 1 is configured to acquire the received acoustic waves originating from the contrast agent 1012 and perform a correction process on the digital signal based on the acquired acoustic waves. Here, when a portion of the contrast agent 1012 enters into a portion other than the circulating blood of the object 15, correction may not be possible in use of a lookup table formed based on the results of measurement of the concentration in the circulating blood. Thus, the photoacoustic apparatus of this example further provides an interest area setting unit to the photoacoustic apparatuses of the respective examples. The interest area setting unit is configured to extract a portion corresponding to a circulating blood segment from the acquired digital signal originating from the contrast agent 1012. In this case, the interest area setting unit is configured to enable a user to designate an interest area in a circulating blood segment of the object 15 via the display unit 20. The interest area setting unit is configured to extract a designated interest area portion from the entire digital signal. By doing so, the photoacoustic apparatus of this example can perform a correction process on only the digital signal originating from the acoustic waves generated from the circulating blood segment. In this way, the correction process can be performed on only the digital signal originating from the acoustic waves generated from a segment in the circulating blood corresponding to a concentration change. Thus, it is possible to acquire even more highly accurate image data and photoacoustic images. However, the interest area setting unit is not limited thereto, but the interest area setting unit may automatically predict a circulating blood segment of the object 15 and automatically set an interest area to the predicted segment.

The interest area setting unit predicts a circulating blood segment automatically using an existing blood flow measurement method such as a Doppler method and sets an area formed from the coordinates corresponding to the predicted circulating blood segment as an interest area. The interest area setting unit extracts a portion of a digital signal corresponding to the interest area set in this manner. In this case, the signal processing module 19a performs a correction process on the extracted portion of the digital signal using a lookup table to generate a correction digital signal. In this case, the image reconstruction module 19b performs image reconstruction on the generated correction digital signal to generate image data. Moreover, the display unit 20 selectively displays the image of the object 15 in the interest area so that the image data is visible. On the other hand, the display unit 20 may not display on the display unit 20, the image data based on the non-extracted digital signal which is based on the acoustic waves originating from the contrast agent 1012 entering into a segment other than the circulating blood segment. Alternatively, the display unit 20 may display a display image based on the image data in the interest area portion in which a correction process was performed so as to be distinguished from a display image based on the image data in a portion other than the interest area. However, the present invention is not limited thereto, but the interest area setting unit may extract data components of coordinates corresponding to the interest area from the entire image data and the display unit 20 may form a display image from the extracted data components.

Example 4

Figure 5:
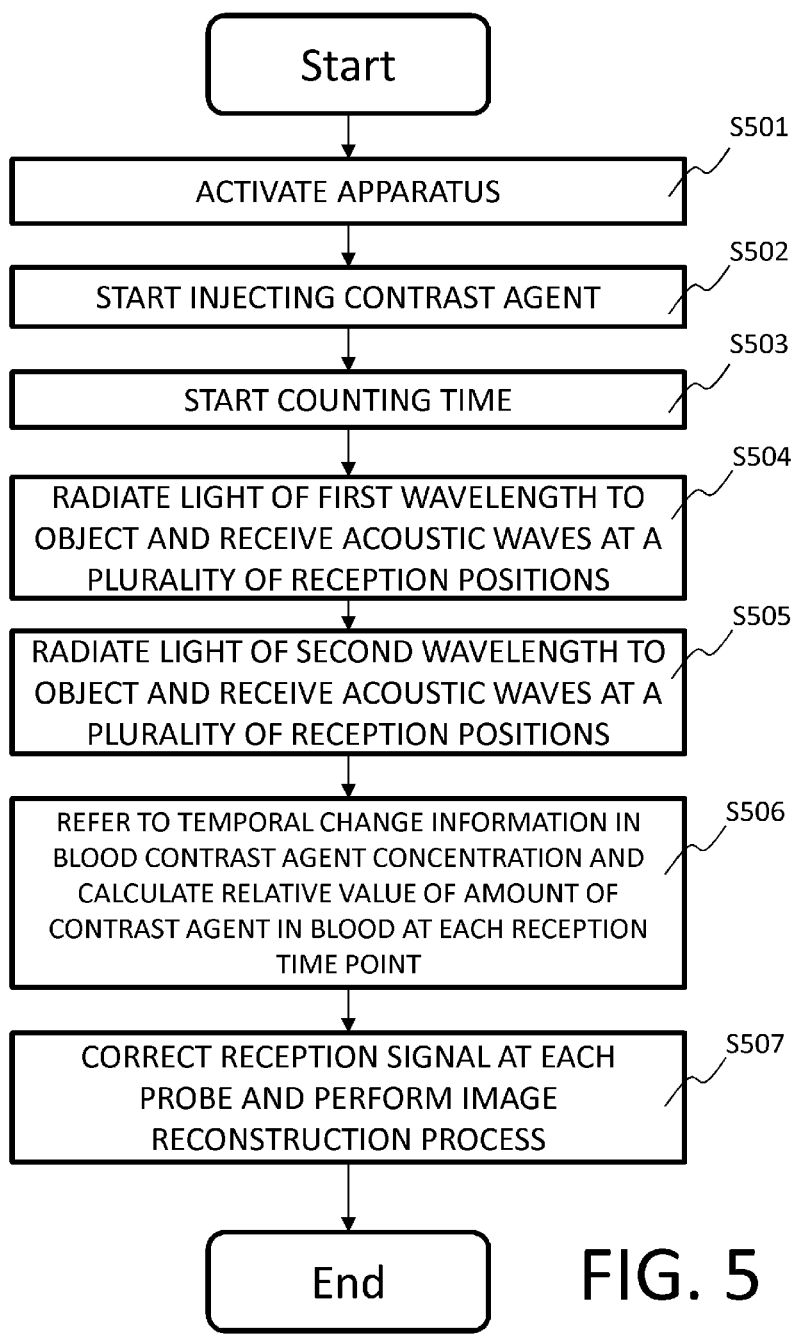
FIG. 5 is a flowchart illustrating Example 4 of the photoacoustic apparatus of the present invention.

FIG. 5 is a flowchart illustrating Example 4 of the photoacoustic apparatus (hereinafter referred to simply as an "apparatus") according to the embodiment of the present invention. In this example, first and second contrast agents having different light absorption coefficients are injected into the object 15. In the apparatus of this example, the light source 11 of Example 1 is configured to be able to output first light having a wavelength selectively absorbed by the first contrast agent 1012 and second light having a wavelength selectively absorbed by the second contrast agent. The processes of steps S501 to S503 of this flow are the same as the processes of steps S301 to S303 of Example 1, and the description thereof will not be provided. When the counting of the elapsed time starts in step S503, the flow proceeds to step S504. In step S504, the first light is radiated according to the same procedure and acoustic waves originating from the first contrast agent 1012 are received as step S304. When reception of acoustic waves at the last reception position ends, digital signals originating from the first contrast agent 1012 at the respective reception positions are generated based on the reception, and are stored in correlation with the reception time of the acoustic waves serving as the source of the digital signals. The probe 17 moves to a predetermined home position and the flow proceeds to step S505. When acoustic waves are received while the probe 17 moves in a spiral form in relation to the object 15, for example, the predetermined home position may be the central position of the spiral trajectory.

In step S505, the probe 17 is moved from the predetermined home position to the first acoustic wave reception position in step S504, the second light is radiated in that state, and acoustic waves originating from the second contrast agent are received. In this case, the procedure of the irradiation and the reception is the same as that of step S304 of Example 1. The digital signals originating from the second contrast agent at the respective reception positions are generated based on the reception and are stored in correlation with the reception time of the acoustic waves serving as the source of the digital signals, and the flow proceeds to step S506. In this case, when the first and second contrast agents are simultaneously injected into the object 15, the reference time of the reception time of the acoustic waves originating from the first and second contrast agents is the time of completion of injection of the first contrast agent 1012 into the object 15. On the other hand, when the second contrast agent is injected into the object 15 after the storage of the digital signals originating from the first contrast agent 1012 is completed, the completion time of injection of the second contrast agent is the reference time of the reception time of acoustic waves originating from the second contrast agent. In any case, the reference time of the reception time of the acoustic waves originating from the first contrast agent 1012 is the completion time of injection of the first contrast agent 1012. The same definition of the reference time is applied to the reference time of first and second lookup tables described later.

The procedure of step S506 is basically the same as that of step S305 of Example 1. However, a first lookup table made up of the reception time points of the first contrast agent 1012 and the concentrations of the first contrast agent 1012 in the blood corresponding to the reception time points is stored in advance in the signal processing unit 19. Further, a second lookup table made up of the reception time points of the second contrast agent and the concentrations of the second contrast agent in the blood corresponding to the reception time points is stored in advance in the signal processing unit 19. The relative value for the first contrast agent 1012 is calculated by referring to the first lookup table. Moreover, the relative value for the second contrast agent is calculated by referring to the second lookup table. After that, the flow proceeds to step S507. In this case, the maximum value of the blood concentration of the first contrast agent 1012 is used as a divisor in the calculation of the relative value for the first contrast agent 1012, and the maximum value of the blood concentration of the second contrast agent is used as a divisor in the calculation of the relative value for the second contrast agent. In step S507, a correction process and an image reconstruction process are performed basically according to the same method as step S306 of Example 1. That is, the digital signals originating from the first and second contrast agents are corrected to form first and second correction digital signals, an image reconstruction process is performed on the first and second correction digital signals to form first and second items of image data, and the flow ends.

By doing so, two types of image data based on acoustic waves originating from two types of contrast agents 1012 can be formed with high accuracy. However, the present invention is not limited thereto, but a light absorber other than the first contrast agent may not be the second artificial contrast agent 1012 but may be a non-artificial light absorber of which the temporal change in a blood concentration is known, for example.

Example 5

A photoacoustic apparatus of this example adds a device (referred to as a change acquisition device) that acquires the temporal change information on the concentration of the contrast agent 1012 in the blood to the photoacoustic apparatuses of the respective examples. In this example, the change acquisition device is driven by the process of step S305 of Example 1. The change acquisition device acquires the concentration of the contrast agent 1012 in the blood at the same time as the reception time of acoustic waves at each reception position. In this case, the change acquisition device generates items of data in which both items of information are correlated for all reception time points, generates change information (a lookup table) on the concentration of the contrast agent 1012 made up of the items of data, and stores the change information in the memory of the signal processing unit 19. The subsequent processes are the same as those of the respective examples. By doing so, a lookup table to be used for correction can be generated easily.

Example 6

A photoacoustic apparatus of this example is the photoacoustic apparatus of Example 3 in which the probe is fixed to an acoustic wave reception position corresponding to an interest area to receive acoustic waves in order to check a temporal change in the concentration of the contrast agent 1012 in a set interest area. The same constituent elements as those of Example 1 will be denoted by the same reference numerals, and the description thereof will not be provided. The photoacoustic apparatus of Example 3 starts counting the acoustic wave reception time and performs the following processes at the first acoustic wave reception time, the last acoustic wave reception time, and an acoustic wave reception time between the two time points. That is, the concentrations of the contrast agent 1012 present in the blood at these respective time points are referred to from the change information (the lookup table) on the concentration of the contrast agent 1012. The relative values of the blood concentrations of the contrast agent 1012 at the respective reception time points are calculated from the change information on the concentration of the contrast agent 1012. A method of calculating the relative values performed in this example may be the same as that of the respective examples. The relative value calculated by the photoacoustic apparatus of this example is used as a conversion coefficient when the digital data at the respective acoustic wave reception time points is corrected similarly to the respective examples. The photoacoustic apparatus of this example corrects the digital data using the conversion coefficient to generate a correction digital signal, and the subsequent processes such as an image reconstruction process are the same as those of the respective examples.

By doing so, the influence on the image data in the interest area due to the temporal change in the concentration of the contrast agent 1012 injected into the living body which is the object 15 is reduced. Further, by acquiring the image data for the interest area in a focused manner, it is possible to acquire more accurate image data in the interest area.

Example 7

Figure 6:
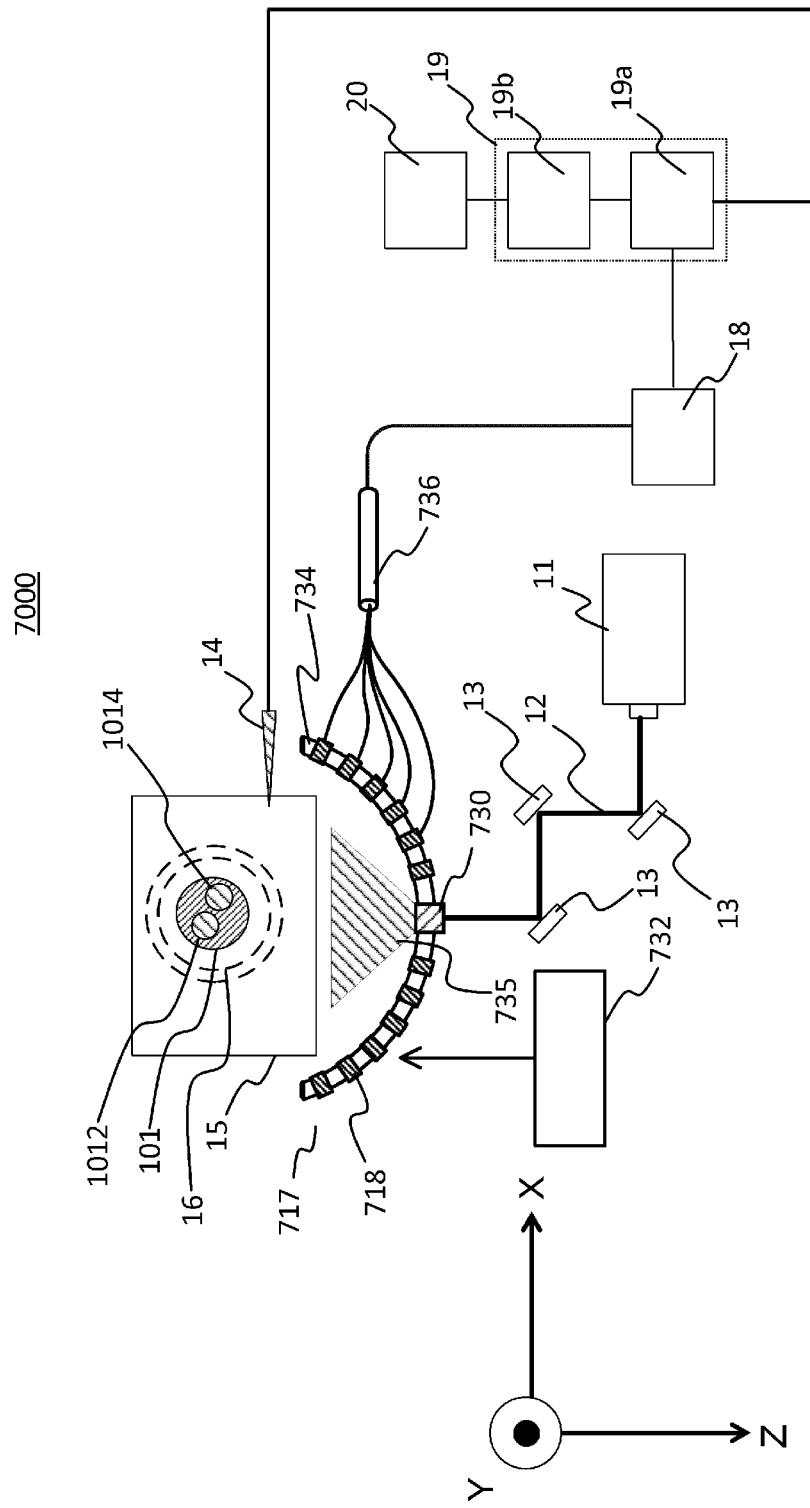
FIG. 6 is a block diagram illustrating Example 7 of the photoacoustic apparatus of the present invention.

FIG. 6 is a block diagram illustrating Example 7 of the photoacoustic apparatus according to the embodiment of the present invention, in which the same constituent elements as those of FIG. 1 will be denoted by the same reference numerals and the description thereof will not be provided unless necessary. Moreover, constituent elements similar to those of Example 1 will be denoted by reference numerals 7xy, in which common numbers are assigned to the ten's digit number (x) and the one's digit number (y) and the description thereof will not be provided unless necessary. A probe indicated by 717 in FIG. 6 illustrates a cross-section cut along line A-A' in FIG. 7. A photoacoustic apparatus 7000 (hereinafter referred to simply as an "apparatus 7000") of this example features in the configuration of the probe 717. The probe 717 has a plurality of acoustic wave detection elements 718 and a holding body 734. The holding body 734 is formed in an approximately hemispherical shape and holds the plurality of acoustic wave detection elements 718 along the approximately hemispherical shape. The acoustic wave detection elements 718 are held so that the directions in which the reception sensitivities are highest concentrate. In this example, the directions in which the reception sensitivities are highest, of the plurality of acoustic wave detection elements 718 are directed to an area that includes the center of curvature of the approximately hemispherical shape of the holding body 734. Electrical signal output ends of the acoustic wave detection elements 718 are connected to signal wires. The electrical signals output by the acoustic wave detection elements 718 are combined by a signal line 736 to which signal wires are commonly connected and are output to the signal collecting unit 18 via the signal line 736. The signals are then processed in the same manner as the respective examples.

An irradiation unit 730 is held at the center of the holding body 734 and is integrated with the probe 717. The irradiation unit 730 radiates light 735 to the object 15 in an opposite direction from Example 1. That is, while the irradiation unit 30 of Example 1 radiates light in a direction (the Z direction in FIG. 1) toward the probe 17, the irradiation unit 730 of this example radiates light (in the negative Z direction in FIG. 6) from the probe 717. The position controller 732 is configured to move the probe 717. The position controller 732 may move the probe 717 in a spiral form, for example. In this case, the irradiation unit 730 integrated with the probe 717 radiates the light 735 at each acoustic wave reception position with the spiral movement by the position controller 732 and the acoustic wave detection element 718 receives acoustic waves based on the irradiation. By doing so, when an acoustic matching solution is provided between the probe 717 and the object 15, the noise in acoustic waves based on vibration of the acoustic matching solution resulting from the movement of the probe 717 can be reduced.

Figure 7:
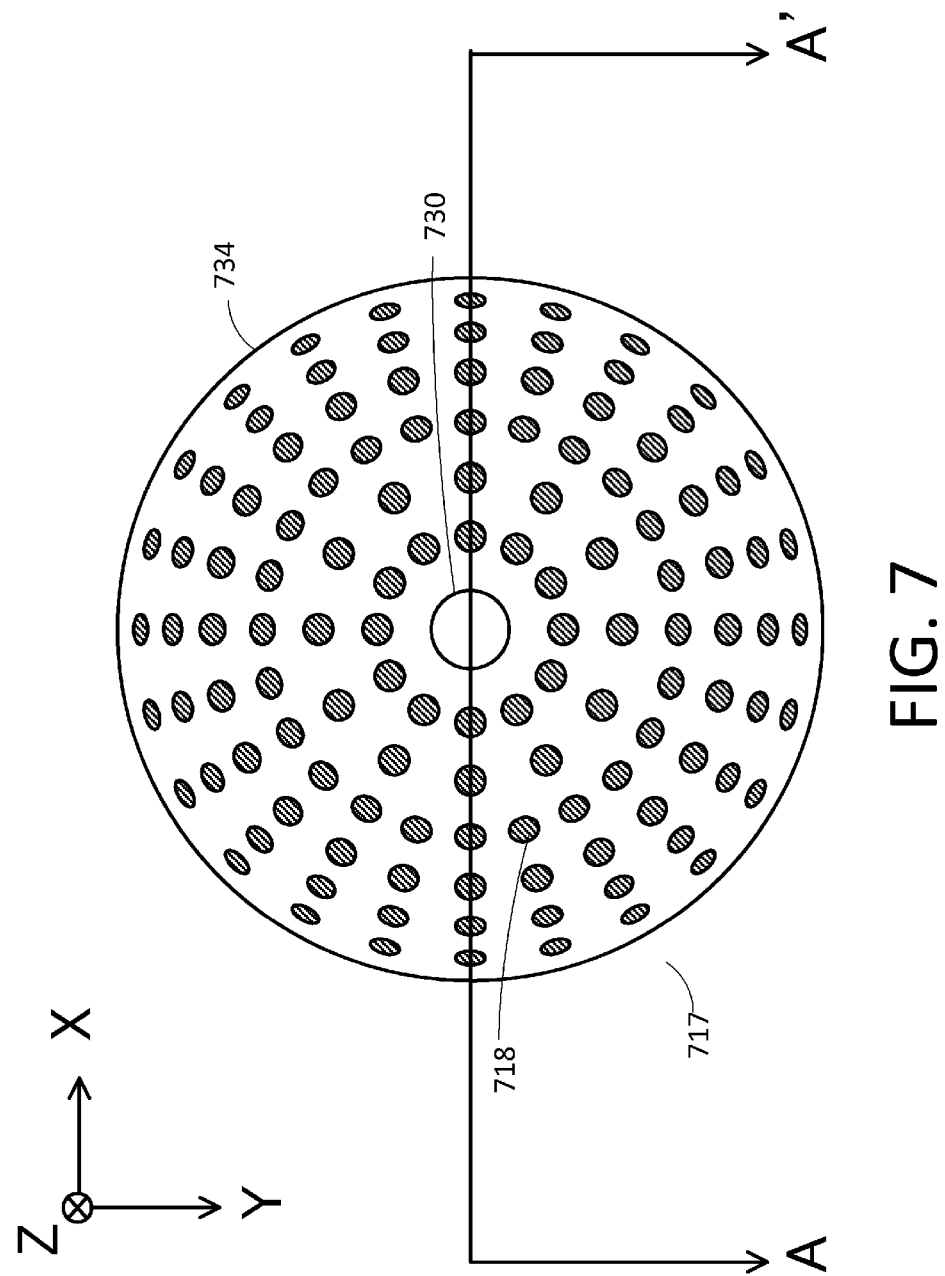
FIG. 7 is a plan view of a probe and an irradiation unit of Example 7 of the present invention.

FIG. 7 is a plan view when seen from the object 15, of the probe 717 and the irradiation unit 730 of Example 7 of the present invention. In the probe 717 of FIG. 7, the acoustic wave detection elements 718 are arranged in a concentric circular form. However, the probe 717 is not limited thereto, but the acoustic wave detection elements 718 may be arranged in a spiral form in the probe 717. The irradiation unit 730 may be provided at the center of the concentric circles of the acoustic wave detection elements 718. Although the light emission end of the irradiation unit 730 is also circular, the shape is not limited thereto but various other shapes may be used. By doing so, it is possible to receive acoustic waves from the object 15 efficiently.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-075393, filed on Apr. 1, 2015, which is hereby incorporated by reference herein in its entirety.

As described above, according to the present invention, a photoacoustic apparatus capable of reducing the influence of a strength variation in acoustic waves based on a measurement period in photoacoustic measurement which uses a contrast agent is provided.

REFERENCE SIGNS LIST

11: Light source
17: Probe
19a: Signal processing module
19b: Image reconstruction module
30: Irradiation unit

What is claimed is:

1. A photoacoustic apparatus comprising:
a light source;
an irradiation unit configured to radiate light from the light source to an object that contains a contrast agent;
a receiving unit configured to receive acoustic waves generated when the contrast agent absorbs the light radiated by the irradiation unit and output an electrical signal;
a correction processing unit configured to correct a signal strength of the electrical signal, based on a temporal change in a concentration of the contrast agent contained in the object; and
an acquiring unit configured to acquire characteristics information on the object, based on the electrical signal that has been corrected by the correction processing unit;
wherein the correction processing unit refers to information related to the temporal change in the concentration of the contrast agent when correcting the signal strength of the electrical signal.

2. The photoacoustic apparatus according to claim 1, wherein
the irradiation unit performs radiation of the light at a plurality of predetermined time points,
the receiving unit receives the acoustic waves at the plurality of predetermined time points and outputs the electrical signal at the plurality of predetermined time points, and
the correction processing unit corrects the signal strength of the electrical signal at each of the predetermined time points.

3. The photoacoustic apparatus according to claim 1, wherein the correction processing unit performs a correction process using a plurality of signal strengths acquired in a time-sequential manner according to the information related to the temporal change in the concentration of the contrast agent when correcting the signal strength of the electrical signal.

4. The photoacoustic apparatus according to claim 3, wherein the information related to the temporal change in the concentration of the contrast agent is formed by correlating the predetermined time point and an estimated concentration of the contrast agent in the object at the time point.

5. The photoacoustic apparatus according to claim 4, further comprising:
an injection unit configured to inject the contrast agent into the object.

6. The photoacoustic apparatus according to claim 5, wherein the correction processing unit refers to the information related to the temporal change in the concentration of the contrast agent by synchronizing the time, at which the receiving unit receives the acoustic waves, and the predetermined time point in the information related to the temporal change in the concentration of the contrast agent, based on a time of completion of the injection of the contrast agent.

7. The photoacoustic apparatus according to claim 6, wherein the correction processing unit acquires the estimated concentration of the contrast agent in the object at the time, at which the receiving unit receives the acoustic waves, by referring to the information related to the temporal change in the concentration of the contrast agent and corrects the electrical signal, based on a ratio of the acquired estimated concentration to the concentration of the contrast agent when the contrast agent has been injected into the object.

8. The photoacoustic apparatus according to claim 7, wherein the concentration of the contrast agent when the contrast agent has been injected into the object is the estimated concentration correlated with an earliest time point among the predetermined time points in the information related to the temporal change in the concentration of the contrast agent.

9. The photoacoustic apparatus according to claim 2, further comprising:
a position controller configured to change a positional relation between the object and the receiving unit,
wherein the correction processing unit corrects the signal strength of each of the electrical signals output by the receiving unit that has received the acoustic waves at the plurality of reception positions when the position controller changes the positional relation, based on the temporal change in the concentration of the contrast agent contained in the object.

10. The photoacoustic apparatus according to claim 9, wherein the plurality of reception positions corresponds to the plurality of predetermined time points in one-to-one correlation.

11. The photoacoustic apparatus according to claim 1, wherein the information related to the temporal change in the concentration of the contrast agent is obtained from a Look-up table which is data related to the temporal change in the concentration of the contrast agent.

12. A photoacoustic apparatus comprising:
a light source configured to radiate light to an object that contains a contrast agent;
an acoustic wave receiving unit configured to receive acoustic waves generated when the contrast agent absorbs the light radiated by the light source and output an electrical signal;
a correction processing unit configured to correct a signal strength of the electrical signal, based on information on a temporal change in a concentration of the contrast agent contained in the object; and
an information acquiring unit configured to acquire characteristics information on the object, based on the electrical signal that has been corrected by the correction processing unit;
wherein the correction processing unit refers to information related to the temporal change in the concentration of the contrast agent when correcting the signal strength of the electrical signal.

13. A photoacoustic apparatus comprising:
a correction processing unit configured to correct a signal strength of the signal output by a receiving unit that receives acoustic waves generated from a contrast agent when an irradiation unit radiates light from a light source to an object containing the contrast agent, by referring to information related to a temporal change in a concentration of the contrast agent; and
an acquiring unit configured to acquire characteristics information on the object, based on the signal that has been corrected by the correction processing unit.

14. The photoacoustic apparatus according to claim 13, further comprising the irradiation unit configured to radiate light from the light source to the object that contains a contrast agent.

15. The photoacoustic apparatus according to claim 14, further comprising the receiving unit configured to receive acoustic waves generated when the contrast agent absorbs the light radiated by the irradiation unit and output the signal.

16. The photoacoustic apparatus according to claim 13, wherein the information related to the temporal change in the concentration of the contrast agent is obtained from a Look-up table which is data related to the temporal change in the concentration of the contrast agent.

17. The photoacoustic apparatus according to claim 13, wherein the irradiation unit performs radiation of the light at a plurality of predetermined time points, the receiving unit receives the acoustic waves at the plurality of predetermined time points and outputs the signal at the plurality of predetermined time points, and
the correction processing unit corrects the signal strength of the signal at each of the predetermined time points.

18. The photoacoustic apparatus according to claim 13, wherein the correction processing unit performs a correction process using a plurality of signal strengths acquired in a time-sequential manner according to the information related to the temporal change in the concentration of the contrast agent when correcting the signal strength of the signal.

* * * * *